US006805732B1

(12) United States Patent
Billiotte et al.

(10) Patent No.: US 6,805,732 B1
(45) Date of Patent: Oct. 19, 2004

(54) ELECTROSTATIC TREATMENT OF AEROSOLS, DEVICES AND METHOD FOR PRODUCING SAME

(75) Inventors: Jean-Marie Billiotte, Neuilly-sur-Seine (FR); Elena Vladimirovna Volodina, Moscou (RU); Alexandre Vladimirovitch Nagolkin, Moscou (RU); Frédéric Basset, London (GB)

(73) Assignee: Airinspace Ltd., Hamilton (BM)

(*) Notice: Subject to any disclaimer, the term of this patent is extended or adjusted under 35 U.S.C. 154(b) by 8 days.

(21) Appl. No.: 10/181,888

(22) PCT Filed: Nov. 23, 2000

(86) PCT No.: PCT/FR00/03300

§ 371 (c)(1), (2), (4) Date: Apr. 9, 2003

(87) PCT Pub. No.: WO01/38000

PCT Pub. Date: May 31, 2001

(30) Foreign Application Priority Data

Nov. 23, 1999 (FR) .......................................... 99 14869

(51) Int. Cl.$^7$ .......................................... B03C 3/155

(52) U.S. Cl. .......................... 96/66; 55/DIG. 5; 95/59; 96/69; 264/129; 264/DIG. 48

(58) Field of Search .............................. 96/2, 3, 65–69, 96/98–100; 95/59, 69, 70, 78; 264/129, DIG. 48; 55/524, DIG. 48; 422/186.04; 204/164

(56) References Cited

U.S. PATENT DOCUMENTS 2,822,058 A * 2/1958 Roos et al. .................... 96/66
3,073,094 A * 1/1963 Landgraf et al. .............. 96/66

(List continued on next page.)

FOREIGN PATENT DOCUMENTS

| | | | |
|---|---|---|---|
| DE | 3802748 | * 8/1989 | |
| EP | 425433 | * 5/1991 | |
| JP | 53-112578 | * 10/1978 | .................... 96/66 |
| JP | 61-249554 | * 11/1986 | .................... 96/66 |
| WO | WO 93/23171 | * 11/1993 | |

OTHER PUBLICATIONS

Mizuno et al; *Journal of Electrostatics,* vol. 25, No. 1, pp. 97–107, Jun., 1990.*

(List continued on next page.)

*Primary Examiner*—Richard L. Chiesa
(74) *Attorney, Agent, or Firm*—Sughrue Mion, PLLC

(57) ABSTRACT

The invention concerns a volume generator (1) of chaotic electrostatic field (E), locally amplified, to subject a fluid (U) loaded with aerosol parties (P, p) to the action of an electrostatic field (E) highly variable in amplitude and orientation locally. This generator (1) includes: an induced electrostatic module (2), consisting of a porous dielectric material (md), two porous electrodes with electrostatic induction (4, 5), an electrical current source (6), and a device for boosting the fluid. The electrostatic module (2) consists of a three-dimensional grid system (Rxyz) having at least locally three-dimensional periodicity (or pseudo-periodicity) in at least three directions. Each grid of the system consists of an externally convex and internally concave elementary cell recessed in its center for including a compact elementary empty cellular volume (V1), that is with transverse dimensions (dx1, dy1, dz1) of the same order of magnitude in the three directions. Preferably, it consists of a plurality of physically and electrically inter-connected fins in the form of a dodecahedral array. The generator (1) is useful for filtering air and in chemistry.

20 Claims, 11 Drawing Sheets

U.S. PATENT DOCUMENTS

| | | | | |
|---|---|---|---|---|
| 3,550,257 A | * | 12/1970 | Brown et al. | 29/592.1 |
| 3,988,131 A | * | 10/1976 | Kanazawa et al. | 96/58 |
| 3,999,964 A | * | 12/1976 | Carr | 96/59 |
| 4,007,024 A | * | 2/1977 | Sallee et al. | 96/65 |
| 4,115,082 A | * | 9/1978 | Newell | 96/17 |
| 4,205,969 A | * | 6/1980 | Matsumoto | 96/66 |
| 4,224,710 A | * | 9/1980 | Solow | 15/22.1 |
| 4,234,324 A | * | 11/1980 | Dodge, Jr. | 96/99 |
| 4,259,093 A | * | 3/1981 | Vlastos et al. | 96/76 |
| 4,284,420 A | * | 8/1981 | Borysiak | 96/40 |
| 4,357,150 A | * | 11/1982 | Masuda et al. | 95/63 |
| 4,509,420 A | * | 4/1985 | Stroffolino | 101/35 |
| 4,759,778 A | * | 7/1988 | Conrad | 96/59 |
| 5,037,455 A | * | 8/1991 | Scheineson et al. | 96/17 |
| 5,108,470 A | * | 4/1992 | Pick | 96/58 |
| 5,198,003 A | * | 3/1993 | Haynes | 96/78 |
| 5,330,559 A | * | 7/1994 | Cheney et al. | 95/63 |
| 5,336,299 A | * | 8/1994 | Savell | 95/70 |
| 5,368,635 A | * | 11/1994 | Yamamoto | 96/17 |
| 5,474,599 A | * | 12/1995 | Cheney et al. | 96/55 |
| 5,484,473 A | * | 1/1996 | Bontempi | 96/65 |
| 5,540,761 A | * | 7/1996 | Yamamoto | 96/67 |
| 5,573,577 A | * | 11/1996 | Joannou | 96/66 |
| 5,609,736 A | * | 3/1997 | Yamamoto | 204/164 |
| 5,807,425 A | * | 9/1998 | Gibbs | 96/66 |
| 5,846,302 A | * | 12/1998 | Putro | 96/66 |
| 5,855,653 A | * | 1/1999 | Yamamoto | 96/58 |
| 5,993,520 A | * | 11/1999 | Yu | 96/66 |
| 6,245,126 B1 | * | 6/2001 | Feldman et al. | 95/59 |

OTHER PUBLICATIONS

References Xd were either cited by applicants in the specification or cited in corresponding PCT Application No. PCT/FR00/03300.*

* cited by examiner

Variations in intensity of the electric field

Variations in angular orientation of the electric field

ELECTROSTATIC TREATMENT OF AEROSOLS, DEVICES AND METHOD FOR PRODUCING SAME

TECHNICAL FIELD OF THE INVENTION

The invention relates to the technical domain of devices for air processing, and more particularly to devices for submitting a fluid charged with aerosol particles (specific dusts or molecules, etc.) to the action of an electrostatic field with high variations of amplitude and orientation, with a view to carrying out a specific electromagnetic action on these particles. This electromagnetic action on the particles can have the aim of mechanical, physical or chemical consequences etc.

The device for generating the electrostatic field according to the invention is of the type constituted of a porous electrostatic module in dielectric material, arranged in sandwich between two porous conducting electrodes, put under different electric voltages, to induce a distribution of charges and an electric field inside the electrostatic module. The charged fluid is pushed through the porous sandwich, in particular using a ventilator. Such devices for electrostatic action on aerosol particles are at present used mainly for electrostatic filtering of particles transported by an air flux. But they use a non-organised electrostatic module in a three-dimensional network and the actual geometry of the cells is random. They implement an electrostatic field which is weakly amplified locally and with small variations of amplitude and orientation.

The electrostatic module of a generator according to the invention is constituted of a meshed network, whose meshes have an organised three-dimensional periodicity and whose mesh cells have a recessed structure, convex externally and concave internally and compact, with a particular repetitive geometry for achieving the required amplification effect and electrostatic field structure.

STATE OF PRIOR ART

The device for amplified electrostatic action according to the invention has much wider applications than those of the domain of filtration. Nonetheless, the closest prior art is essentially constituted of electrostatic filters for dusts. Consequently, the analysis of prior art given below is restricted to this technical field and more generally to the different techniques for filtering dusts.

For medical, sanitary and air purity reasons, it is advantageous to filter the small particles in the air and in particular industrial dusts, pollens, bacteria, viruses, fungi, algae and other fine dusts. Apart from systems operating using gravitation (settling of particles due to their weight) and cyclone systems operating through the effect of centrifugal forces (both of them used together in certain specific industrial applications, resulting in systems with large overall dimensions), the two most common methods for ensuring decontamination of dust particles in the air comprise:—one to block the air flow with the aid of a medium (mechanical filter);—and the other to deflect and capture the dusts using an electrostatic method (electro-filter).

According to the first method with a mechanical filter, the air passes through a porous filtering medium. A distinction can be made between: mechanical filters with surface filtration; and mechanical filters with in-depth filtration.

In the case of surface-effect mechanical filters, the medium is generally constituted of a sheet of woven metallic threads, a meshed material, a paper filter, a membrane etc. The medium has surface pores or holes. The size of the pores in the medium is chosen such that the air passes through whereas, because of their size, the "big particles" are captured and held on the fibres or material of the medium. Although, in practice, mechanical filters rarely have holes smaller than the size of the particles they have to capture, they act as if they had. The particles are captured progressively on the edges of the holes and tend to create a porous wall bridging the hole by agglutination. The collected particles cling together on the surface of the filtering medium and progressively constitute a "cake" of increasing thickness. Thus, with use, the "cake" of collected particles becomes the filter and the initial medium becomes the filter support.

In the case of mechanical filters with in-depth filtration, the particles do not only form a coherent surface cake, but the particles are caked to a certain depth in the vicinity of the surface of the medium. An example of such a filter is constituted by cigarette filters. The medium has a certain thickness and its fibres are not woven to form a surface, but are collected together in thickness according to more or less random directions. When the fluid meets a fibre placed approximately transversal, the flux is deflected around the fibre, but part of the particles, denser than the gas, have a tendency to be deflected less. They hit the fibre instead of following the gas. The separation of dusts is carried out by inertial impact on the fibres. The captured particles are then partly kept in place according to Van der Waals electrostatic forces.

In applications requiring high filtration efficiency, such as sterile rooms, a variant of the mechanical filter is used, applying folded filtering medium cartridges, called high efficiency filters (HEPA) or very high efficiency filters (ULPA).

The second method, with an electrostatic filter or electro-filter, is based on the fact that particles with a certain charge are attracted by a collector electrode of the opposite charge. This method has been used widely in industry since its invention by F. G. Cottrell in 1910. Preliminary means are used to give an electrostatic charge to the particles and, using an electrostatic field, these charged particles can be precipitated on a collecting wall or a collecting medium maintained at a voltage of the opposite sign. There exist two principal classes of electrostatic filter structures:—those with one stage,—and those with two stages. There also exist two variants of electrostatic precipitation means:—those with electrodes under voltage generated externally by electrical supply,—and those with electrostatic self-charging, charged by air friction.

Single stage electro-filters, or filters charged electrostatically, are produced according to the self-charging variant, according to which their filtering medium accumulates an electrostatic charge resulting from the passage of the air flux through the medium constituting them. In general they also use the fact that the particles are previously charged electrostatically from air friction. They are of low cost and of low efficiency.

Two stage electro-filters, also called electrostatic precipitators, are of higher complexity, cost and efficiency. They comprise a stage of electric charging of the particles by corona effect plus a precipitation stage. In the electric charging stage, the air passes through an ionisation zone constituted of one of several wires set at high voltage to generate an intense electrostatic field, within which the particles are electrically charged by ionisation. Then the air flux comprising the charged particles passes through a second collection stage. There are two types of two-stage electrostatic filters, depending on the structure of the collector stage for charged particles (—with plates,—or with a filtering medium).

According to the first type of electrostatic filter, with parallel plates but with electric field transversal to the flux (used in particular for treating industrial gaseous effluents), the collector is formed of an alternate parallel plurality of plates under high voltage and earthed plates, oriented parallel to the air flux. The charged particles are deflected perpendicularly to the flow path because of the transversal electric field, perpendicular to the plates and thus to the flow. As a result, the particles are precipitated onto the plates.

According to a second type of electrostatic filter, with filtering medium, the collector stage is constituted of one or several grids or porous electrodes (generally put under alternating voltages) and separated by plates of a filtering porous collector medium. The grid and the plates are located perpendicular to the air flow. The field is closely longitudinal or slightly inclined relative to the path of the fluid. This type of electro-filter is used principally for domestic purposes, especially in the field of air conditioning and central heating.

Among the different types of known filters and more generally among the electrostatic systems of prior art, the electrostatic filters with transversal medium, and as an auxiliary the in-depth filtration mechanical filters, are structurally the closest to the electrostatic device according to the invention.

A first major disadvantage of mechanical or electrostatic filters with a filtering medium is that the smallest particles and in particular the microbial particles (bacteria and viruses) pass through the pores, such that the efficiency of the mechanical filters diminishes considerably in function of the size of the particles treated.

Thus, in order to filter very small size particles, in particular bacteria and viruses, the size of the pores has to be reduced in the same proportion or the fibres have to be made denser. There is consequently a significant loss of pressure load during passage through the filtering medium, which brings about a considerably higher energy consumption.

This means that a second disadvantage of mechanical or electrostatic filters with a filtering medium is that they produce a loss of charge and high energy consumption.

A third disadvantage of mechanical or electrostatic filters is the fact that the filtering efficiency of physical methods implementing the filtering media (whether they operate by impact, diffusion or electrostatic effect) is poor. This means that the porosity of the filtering media (pore size) must be of the same order of size or, in all cases, must be sufficiently low relative to the size of the particles to be filtered. Consequently, the filtering media used have a low porosity ratio (empty pore volume for filtering material volume). This is disadvantageous and brings about:—low in-depth efficiency,—a low retention volume compared with the thickness of the medium, and thus compared with the resulting loss of charge,—and rapid clogging of the pores which quickly makes the filtering medium filter inefficient.

A fourth disadvantage of filtering medium filters, whether they be mechanical and of "surface effect" or "in-depth" effect or electrostatic, is that they retain the large particles more on the surface than in depth. They act essentially on the surface or over a small thickness near the input face. They quickly form—either a surface "cake"—or a layer of big dusts, clinging against the fibres, of density decreasing with the depth of the medium which, in the two cases, progressively blocks the porosity of the medium, reduces the cross-section of the pores considerably, increases the loss of charge and reduces the flow rate and the efficiency of the filter.

A fifth disadvantage, resulting from the preceding disadvantages, is that the filtering media need complete cleaning of the medium or frequent changing of this medium (HEPA or ULPA filter cartridges . . . ). This is both expensive and very difficult to implement reliably. This is the case, in particular, for food industry factories, or hospitals, where a large number of filters must be maintained or have their medium changed regularly because of progressive clogging.

A sixth disadvantage of filtering medium filters is their low reliability. In fact, the efficiency and blocking of filtering media are very sensitive to the ambient air, in particular its humidity and the particle concentration. These parameters are often random and in practice very difficult to take into account in evaluating the regularity of maintenance required.

A seventh disadvantage, related to electrostatic filters, whether they be of the plate or filtering-medium type, is linked to the deposit of big particles on the electrodes or on the active parts of the filtering medium, with consequent progressive lowering of the efficiency of the filter by dielectric effect (as described below). The result of particle deposit is the progressive formation of a dielectric surface film of dust. The adhesive forces of electrical cohesion must be sufficient to prevent these particles being drawn into the air flux. One of the properties of the dust layer, which is extremely important for the operation of an electro-filter, is the electrical resistance of this layer. Because of the very wide spectrum of the filtered particles, the electrical resistance can vary from 10exp−3 to 10exp14 ohm.cm. When the resistance is very low (less than 10exp4 ohm.cm), there is very rapid movement of charges between the dusts deposited on the conducting plate. Insufficient electrostatic charge remains within the particles collected, to hold them. This results in frequent re-collection of the particles and the efficiency of the electro-filter suffers. On the other hand, if the efficiency of the dust-film is too high and greater than 10exp10 ohm.sec, the efficiency of the electro-filter is reduced considerably. In fact, a large fraction of the variation in electric potential takes place across the high resistance dust film and not in the air. The particles are attracted less because of this lowering in voltage. Furthermore the electric resistance of the layer varies with time. Consequently, an eighth disadvantage of electrostatic filters with plates or a filtering medium is that their electrostatic efficiency diminishes with time.

A ninth disadvantage of electrostatic air filters with filtering medium, according to prior art, is that they do not enable spatial selectivity of capture of particles according to their size, meaning that particles of any size are captured almost uniformly in each zone of the medium. The big particles (and the small ones) are deposited uniformly over the capturing surface of the filtering medium. Progressively, the small particles and also the big ones are (uniformly) captured less and less. In other terms the filtering of the small particles is hindered by the fact that the medium is encumbered by the big particles. When the air comprises a large spectrum of particle sizes, the action on the small particles is rendered inefficient progressively because of blocking by the big particles.

It is well known in prior art how to place porous filtering media sandwiched between two porous electrodes set at different voltages with the aim of creating an electric field inside the filtering medium, and how to make a flux of air loaded with particles pass perpendicularly through the sandwich. This is the classic structure of the collection stage of an electrostatic air filter with transversal medium. The U.S. Pat. No. 3,999,964 describes an electrostatic air filter with transversal medium of this type, comprising a medium constituted of a porous material sandwiched between two V-shaped and perforated surface grids. One of the grids is set at a voltage of 6000 V whilst the other is earthed. The air is forced through the sandwich constituted by the two grids and the medium. U.S. Pat. No. 5,108,470 also describes a system of this type. Such a system is also described in the U.S. Pat. No. 5,330,559. An application of this technique is also described in the European patent WO 93/23171 in the name of the inventors.

U.S. Pat. No. 5,368,635 and U.S. Pat. No. 5,540,761 describe such a system in which, furthermore, the particularity is to slow down the gas at the level of the medium, in such a way as to allow a greater transversal movement of the particles, in order to raise capture efficiency and to make it possible to increase the size of the pores by thus limiting the speed of clogging of the pores by the dusts. In a variant it is recommended to use a medium constituted by association of conducting and/or insulating fibres placed at random in such a way as to provide holes in which "intense fields" develop. Different types of materials are suggested (paper, glass fibre, natural fibres, . . . ) whose structure is essentially random, meaning without any defined geometric organisation.

It is also known in prior art how to constitute an electro-filter with transversal medium by passing a flux of air loaded with particles through a porous collecting medium, self-charged electrostatically (one stage electro-filter), where the collecting medium comprises an assembly of channels constituted by the random structure of the medium in cellular foam material. In particular, it is known how to use a synthetic foam with open cells as filtering medium. Thus, to constitute an electrostatic filter, the U.S. Pat. No. 4,115,082 proposes placing two adjacent sheets, made of "synthetic foam with open cells" to cover the assembly with two films of synthetic resin fibres capable of maintaining a negative charge, and to place the whole assembly between two series of acrylic plastic rods capable of developing a positive electrostatic charge. U.S. Pat. No. 5,336,299 describes a self-charged electro-filter of the same type, whose filtering medium is constituted of a "central film in Plexiglas honeycomb weave".

Prior art is not concerned either by the particular overall geometry of the mounting of the cells of the porous material used (periodicity) or the internal organisation of each of these cells (geometry).

Thus, the U.S. Pat. No. 4,115,082 recommends using "a foam with open cells in polyurethane" without referring to the importance of the particular geometry or the organisation of the cells. The same applies to the U.S. Pat. No. 5,336,299.

It is known how to pass the fluid through parallel channels with wide elongated rectangular cross-section. An electro-filter of this type is described in the U.S. Pat. No. 4,007,024. The passage channels are provided between a plurality of elongated parallel collector plates separated from each other and including an ionising wire in the centre. An equivalent system is described in the U.S. Pat. No. 5,198,003. An equivalent system is also described in U.S. Pat. No. 5,484,473.

It is known how to make the fluid pass close to elongated parallel plates which can be described as "wings" inclined relative to the path of the fluid and provided with tapered trailing edges. U.S. Pat. No. 4,007,024 describes such parallel plates provided with tapered trailing edges, arrow shaped, in such a way as to deflect and slow down the fluid. These "wings are not set in a three-dimensional manner but two-dimensionally.

It is known in prior art how to use a "honeycomb" material as collector medium constituted of parallel channels which can be called parallel open elongated cells. U.S. Pat. No. 4,205,969 proposes placing a collector medium constituted of one or several plates of a "honeycomb" dielectric material between two metallic electrodes, also in "honeycomb". The "honeycomb" material is constituted of elongated parallel channels opening into each other, along the axis of the fluid or slightly inclined. Such a particularity is also described in the U.S. Pat. No. 3,988,131. These cells have a two-dimensional and not a three-dimensional repetitiveness.

It is known how to make a fluid pass between wide and long parallel plates, submitted to differences in voltage. An electro-filter with two stages and with a plate of this type is described in the U.S. Pat. No. 4,259,093. In this case the repetitiveness is one-dimensional.

It is known how to give the filtering medium the form of a layer with a fine open structure, in woven wires. The U.S. Pat. No. 5,037,455 proposes such a structure made of woven polypropylene. This medium does not provide—cells.

It is known in prior art how to use, as collector surface, an assembly of very elongated parallel channels in the form of tubes, placed between the electrodes; the channels and the electrodes being parallel to the movement of the fluid. The U.S. Pat. No. 4,234,324 proposes such a structure. U.S. Pat. No. 5,198,003 also describes a similar structure as does the U.S. Pat. No. 4,284,420.

It is known how to place a fine filtering medium of the HEPA type between live electrodes to increase filtering efficiency. This is described in the U.S. Pat. No. 4,357,150 and the U.S. Pat. No. 4,509,420.

It is known in prior art how to place a micro-porous powder material arranged according to random geometry between two electrodes at different electric potentials and to make a fluid loaded with particles pass through. Such a device is described in the U.S. Pat. No. 4,224,710 in which the micro-porous powder material is constituted in particular of charcoal.

It is known in prior art how to submit a fluid to a tortuous passage, through a porous dielectric material placed between two live electrodes and to operate locally inclined fields within this dielectric. Such a device is described in the U.S. Pat. No. 4,759,778.

It is known how to provide the electrodes of an electro-filter with filtering medium with points but with the aim of encouraging ionisation of the air particles. This is described, in particular, in the U.S. Pat. No. 5,573,577. But prior art does not take into consideration the particular combination between electrodes with points co-operating with a special geometry of the filtering medium, also with points, to increase the field effect within the medium.

BRIEF DESCRIPTION OF THE INVENTION

The invention relates to a volume generator of chaotic electrostatic field, ensuring local amplification of the electrostatic field, to submit a fluid loaded with aerosol particles to the action of an electrostatic field with high local variation in amplitude and orientation.

An electrostatic field generator according to the invention is of the type known in prior art comprising:

an induced electrostatic module, constituted of a porous material, two electrostatic inducing electrodes placed facing each other, separated from each other, on either side of the electrostatic module, a source of electric current, at least two conductors connecting the terminals of the source to the electrodes, and a means for putting the fluid at overpressure to ensure its flow through the electrodes and the electrostatic module.

In certain applications, one can add an ioniser upstream from the generator to pre-charge the particles electrically and to increase their interaction with the electrostatic field generated.

The invention relates principally to an improvement of the constitutive structure of the electrostatic module of the electrostatic field generator. In its general embodiment, the invention recommends using an electrostatic module constituted of a network of three-dimensional meshes showing (at least locally) a periodicity (or pseudo-periodicity) in three dimensions (in at least three directions). According to the invention, each mesh of the three-dimensional network is constituted of an externally convex elementary cell, recessed at the centre and therefore concave internally, to include a compact elementary empty cellular volume. This means that the transversal dimensions of the cellular volume are of the same order of size in the three directions. According to the invention, the elementary empty cellular volume of the majority of the cells located at the centre of the electrostatic module open out facing elementary empty volumes of neighbouring cells by at least four recesses through their elementary surface.

According to a preferred embodiment of the invention, the electrostatic module is constituted by assembling a plurality of fins with longilineal portions, constituted of a dielectric or semiconducting material. The fins have a fine, not very wide, transversal cross-section, of a much lower thickness than their longitudinal dimension, and comprise at least one lateral trailing edge, elongated and tapered. The fins are physically and electrically connected together by each of their extremities to constitute a dielectric three-dimensional network. In the three directions, the network can have either a strictly repetitive mesh or a quasi-repetitive mesh (quasi-network). The fins are associated and regrouped geometrically in order to constitute a multiplicity of elementary cells (network meshes). The majority of the interior fins of the electrostatic module are common to several elementary cells.

According to this preferred variant of the invention, the majority of the associated fins, belonging to a same internal cell of the electrostatic module, surround and juxtapose tangentially, along at least one of their lateral longitudinal faces, an elementary surface including an elementary empty cellular volume.

An important variant of the invention is that the internal elementary volumes of the cells have a convex and compact structure. By compact, it is understood that the transversal dimensions of elementary cellular volume are of the same order of size in the three geometric directions. By convex, it is understood that in the geometric mathematical meaning of the term the elementary volumes have an overall form close to a strict or slightly deformed ball, to an ellipsoid or to a regular and non-elongated parallelepiped volume, such as for example—a tube—or a non-structured volume such as that constituted by the interstices embodied between a multitude of fibres regrouped at random. Finally, the communicating recesses between neighbouring cells are surrounded by the lateral edge of fins belonging to its cell and common to those 'of the neighbouring cells.

An electrostatic field generator according to the invention comprises, within its electrostatic module, a three-dimensional plurality of zones of electrostatic induction, distributed over three-dimensional, periodic or pseudo-periodic networks. In the preferred embodiment according to the invention described above, the induction zones are located closely around the cellular volumes and in the vicinity of the trailing edges of the fins, at the interface between the cells.

These electrostatic induction zones crossed by the particles have high local variations of electrostatic field relative to the average intensity evaluated over the totality of the electrostatic module, and/or high variations of orientation of the electrostatic field relative to the average electric field orientation, evaluated over the totality of the electrostatic module.

DRAWINGS AND FIGURES

DETAILED DESCRIPTION OF THE IMPLEMENTATION OF THE INVENTION

Figure 1:
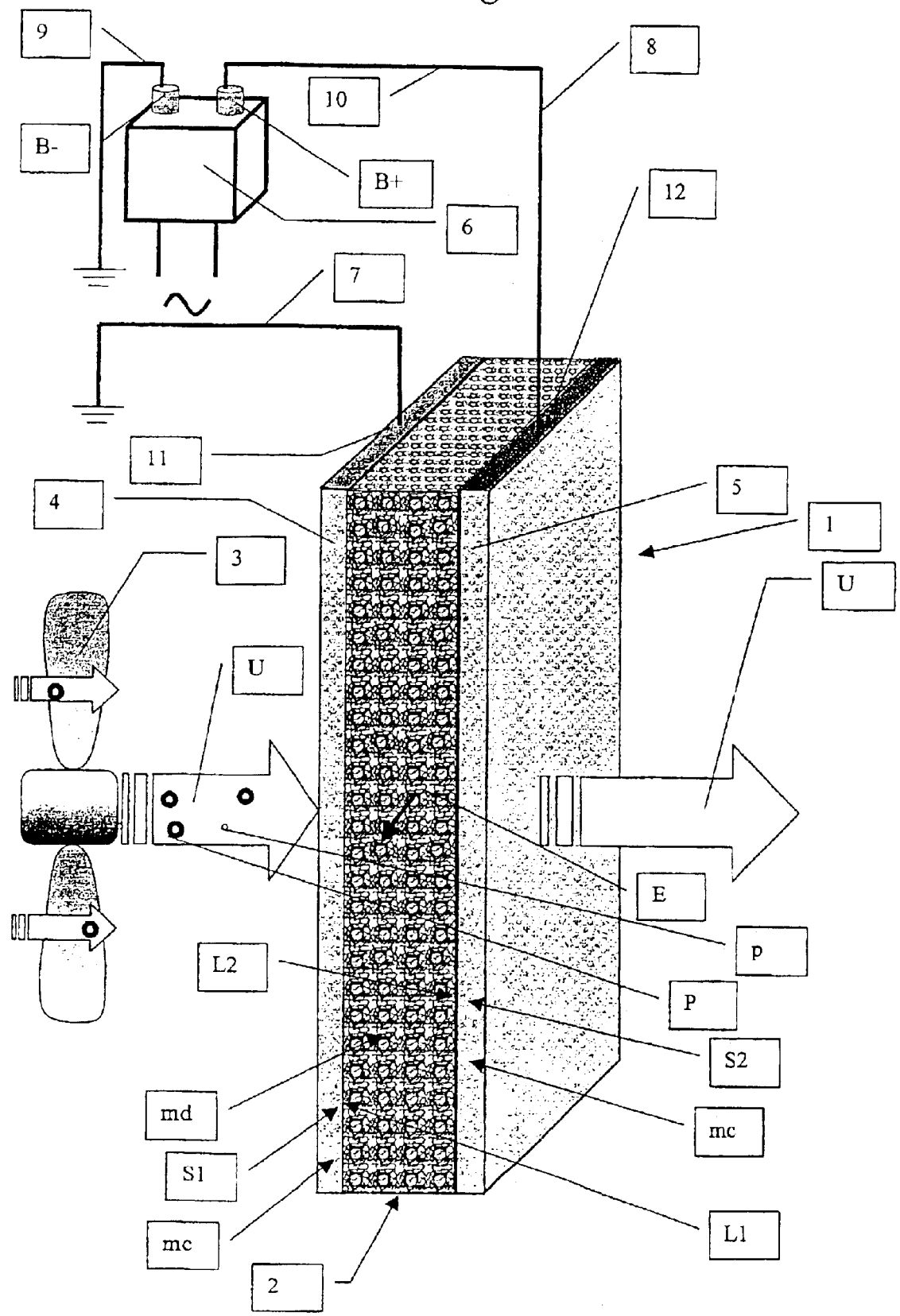
FIG. 1 shows globally the different elements constituting an electrostatic generator according to the invention.

With reference to FIG. 1, the general constitution of an electrostatic generator 1 according to the invention can be seen.

The volume generator 1 of chaotic electric field (E=E1, E2, E3, . . . ) is constituted in the classic manner of an induced electrostatic module 2, of two electrostatic induction electrodes 4, 5, placed facing each other on either side of the electrostatic module 2, of a source of electric current 6, and of two conductors 7 and 8 connected to the electrodes 4, 5, and to the current source 6.

The electrostatic induction module 2 is constituted of a dielectric or semiconducting material (md). Preferably, it has a flat shape and a porous internal geometry permeable to the passage of fluids U. On either side, it has at least two lateral contact surfaces L1 and L2 facing each other.

Its two electrostatic induction electrodes 4, 5, are constituted of a conducting material (mc). Preferably they are flat in shape. Their geometry is porous and permeable to the passage of fluids U. They are set facing each other, separated from each other, and are in contact on either side of the electrostatic module 2. Each of them co-operates through one of their lateral support faces S1, S2, with one of the two lateral contact faces L1, L2 of the electrostatic module 2.

The electric current source 6 comprises at least two metallic terminals B+, B−, with a fairly high potential difference between them. For dust filtering applications, the invention recommends using a current source generating voltages of B+=+5000V and B−=−5000V.

The two electrical conducting wires 7, 8, are each connected by one end 9, 10, to one of the voltage terminals B+, B− and/or earthed, and at the other end 11, 12, to one of the electrodes 4, 5, of different polarisation. In the variant shown, one of the two conductors 7 is constituted partially by the earth G.

Figure 5:
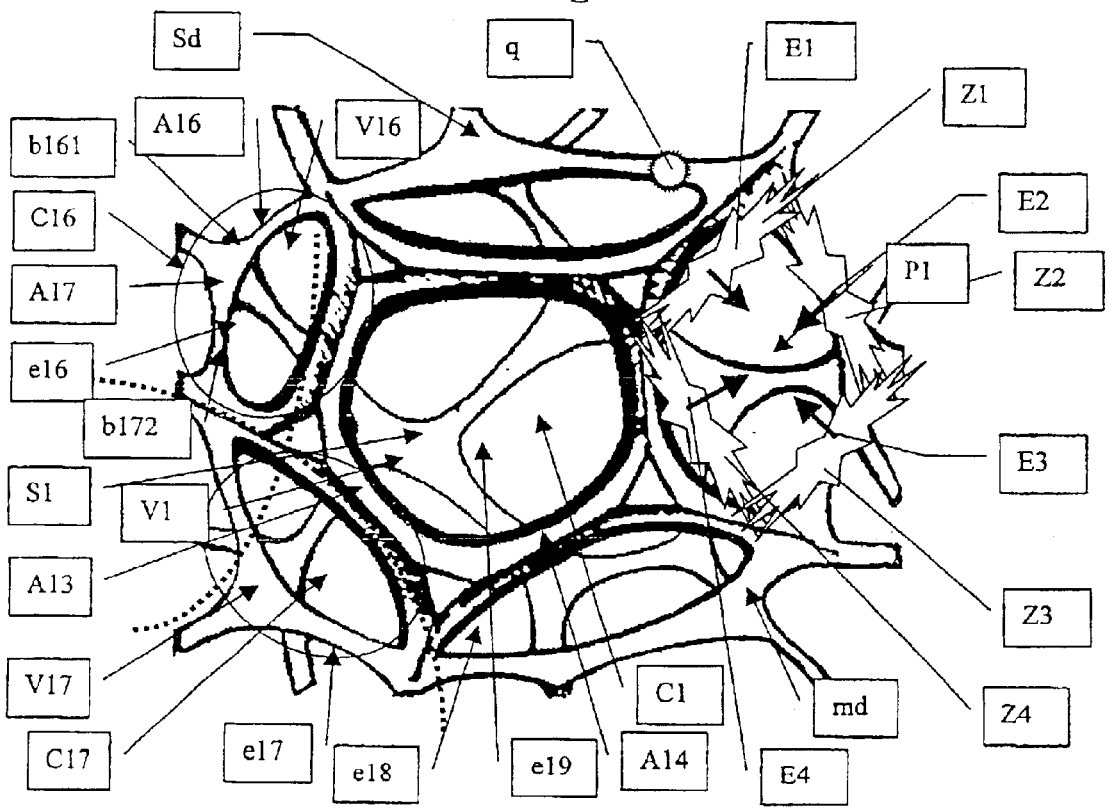

In this way, and as shown in FIG. 5, between the two electrodes 4, 5, and thus within the polarisable module 2, one creates a distribution of charges q over the surface Sd of its constitutive material md. As a result, one creates a volumic distribution of the internal electric field E.

An axial ventilator 3 is used as a means for putting the fluid U at overpressure in order to ensure that it flows through the sandwich constituted of electrodes 4, 5 and the electrostatic module 2.

Figure 2:
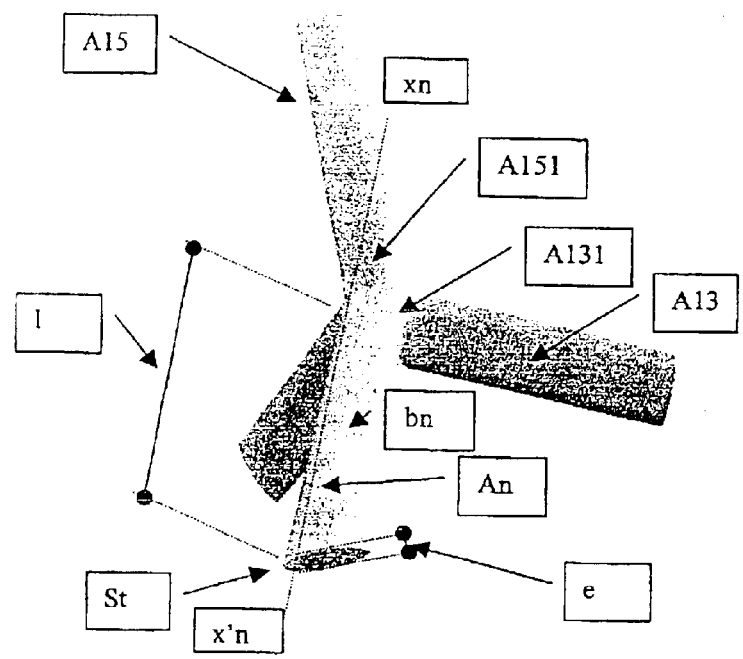
FIGS. 2 and 3 show a fin assembly according to the preferred embodiment of the invention to constitute the three-dimensional network structure and its electrostatic module.
Figure 3:
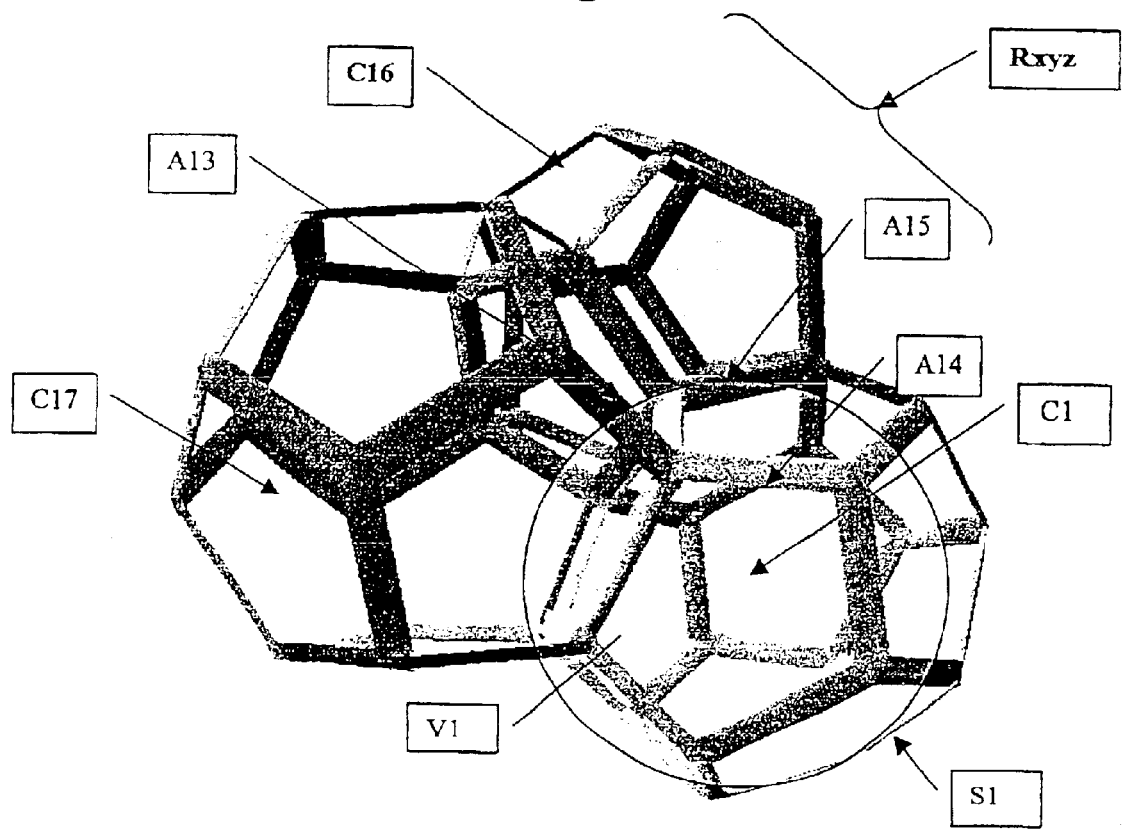

The preferred variant of the invention for producing the volume generator 1 of chaotic electrostatic field E according to the invention is shown in FIGS. 2 and 3. The electrostatic module 2 is constituted of a plurality of fins A =( . . . , A13, A14, A15, . . . , An, . . . ) with longilineal portions, constituted of a dielectric or semiconducting (md) material. The fins An have a fine transversal cross-section St, not very wide, and a thickness e very much lower than their longitudinal dimension l. They comprise at least one lateral trailing edge bn, elongated and tapered, and oriented in the direction xn, x′n along the length of the fins.

Figure 7:
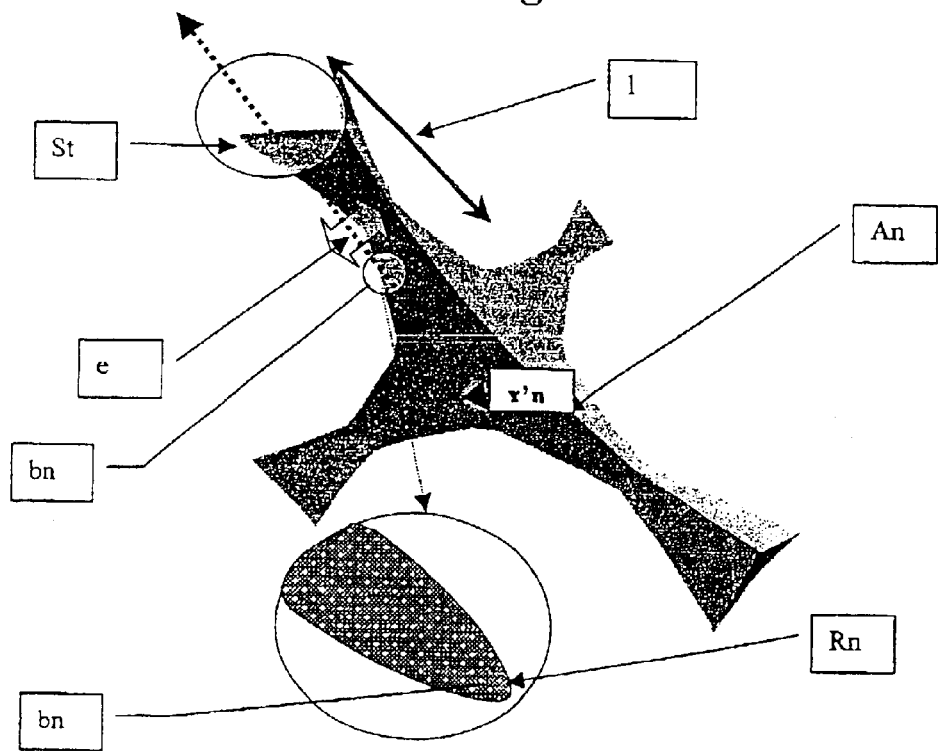
Figure 8:
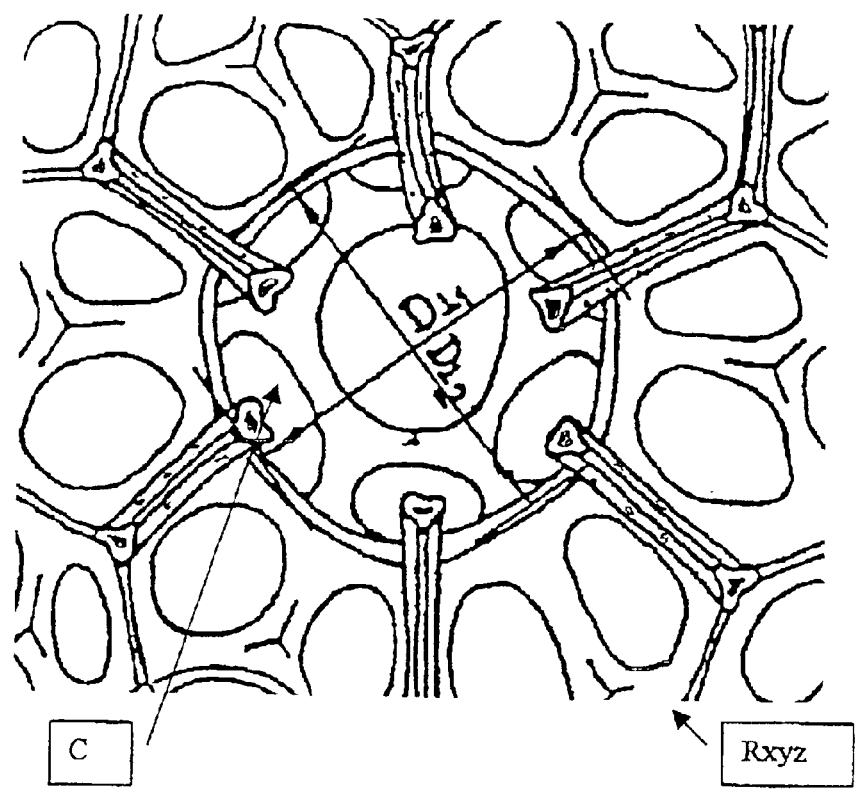

As shown in more detail in FIG. 7, in a particular embodiment of the invention, a transversal cross-section of the fin An has, in the vicinity of its trailing edge bn, a small transversal local radius of curvature Rn.

It can be seen with reference to FIGS. 3 to 6 that the fins ( . . . , A13, A14, A15, . . . , An, . . . ) are connected to each other physically and electrically by each of their ends (A13_1, A13_2, A14_1, A15_1, . . . ) to constitute a three-dimensional dielectric network (Rxyz). They are associated and regrouped geometrically to constitute a multiplicity of elementary cells (C1, . . . , C16, C17, . . . ). The interior fins A13 of the electrostatic module 2 are in the majority common to several elementary cells ( . . . , C1, . . . , C17, . . . ).

Figure 4:
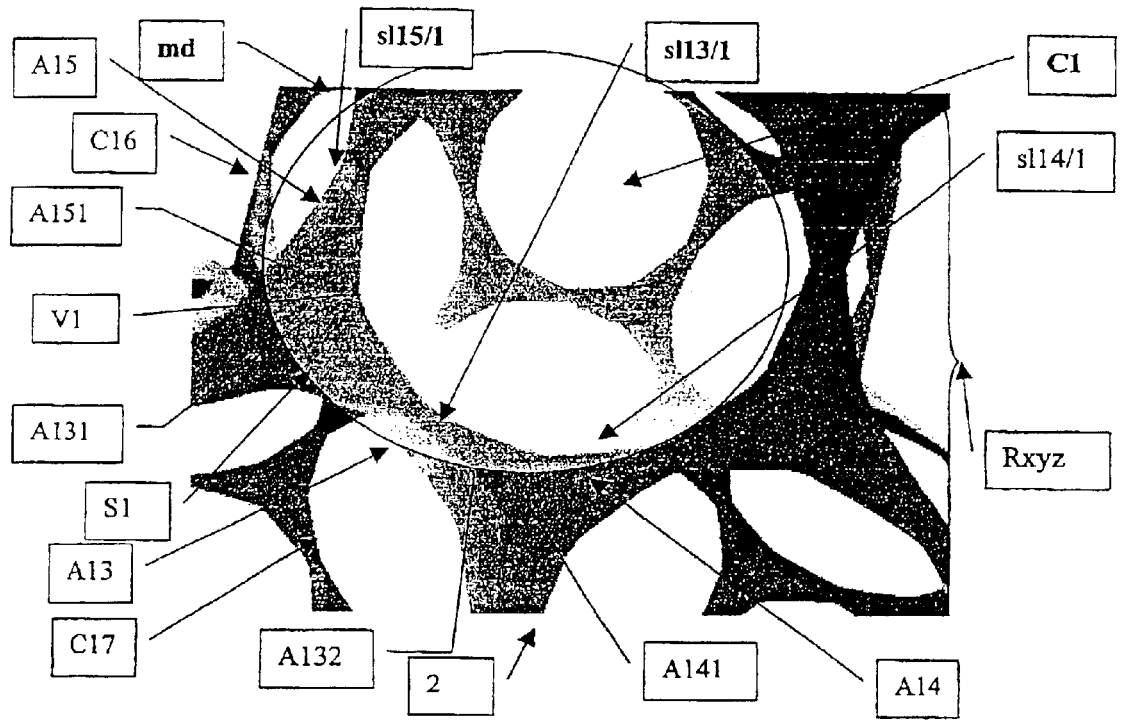
FIGS. 4 and 5 show the constitutive particularities of a mesh of the electrostatic module network.

FIGS. 4 and 5 show that the majority of the associated fins ( . . . , A13, A14, A15, . . . ) belonging to a same interior cell C1 of the electrostatic module 2 surround and juxtapose tangentially, along at least one of their lateral longitudinal faces (s1 13/1, s1 14/1, s1 15/1, . . . ),one virtual elementary surface alone S1 interior to each elementary cell C1. The cells (C1, . . . ) are globally convex externally and concave internally.

Figure 6:
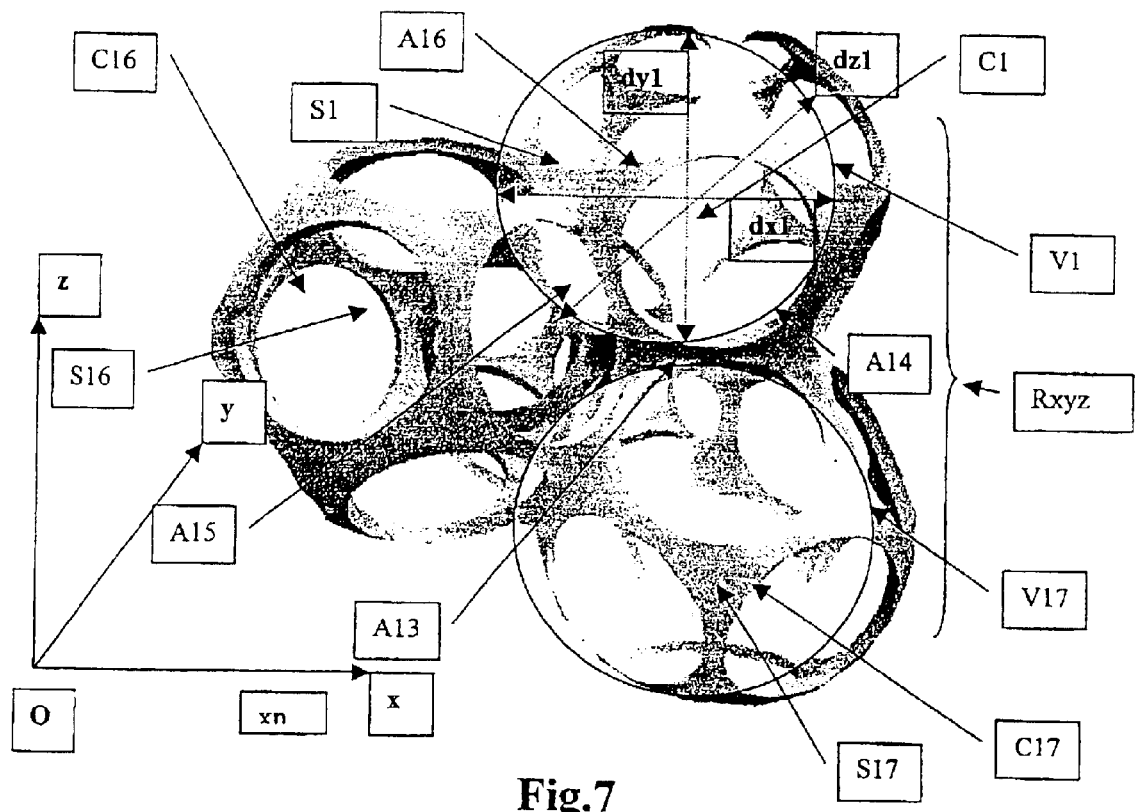
FIGS. 6 to 8 and 10 show the organisation of a network type of the electrostatic module according to the invention, obtained by intersection of thin-walled spheres.

With reference to FIGS. 4 to 6, it appears that the geometry of this elementary surface S1 is closed, to include an elementary empty cell volume V1, externally convex and internally concave and compact. This means that the transversal dimensions dx1, dy1, dz1, of a cell volume V1 are of the same order of size in the three geometric directions x, y, z.

With reference to FIG. 5, it is seen that the elementary empty cell volume V1 of the majority of cells C1 located at the centre of the electrostatic module 2 open out facing elementary empty volumes (V16, V17, . . . ) of neighbouring cells (C16, C17, . . . ) by at least four recesses (e16, e17, e18, e19, . . . ) through their elementary surface S1. With reference to FIG. 3, it is seen that each of the recesses e16 is surrounded by the lateral edge (b161, b172, . . . ) of fins ( . . . , A16, A17, . . . ) belonging to its cell C16 and common to the neighbouring cells (C16, C17, . . . ).

Figure 14:
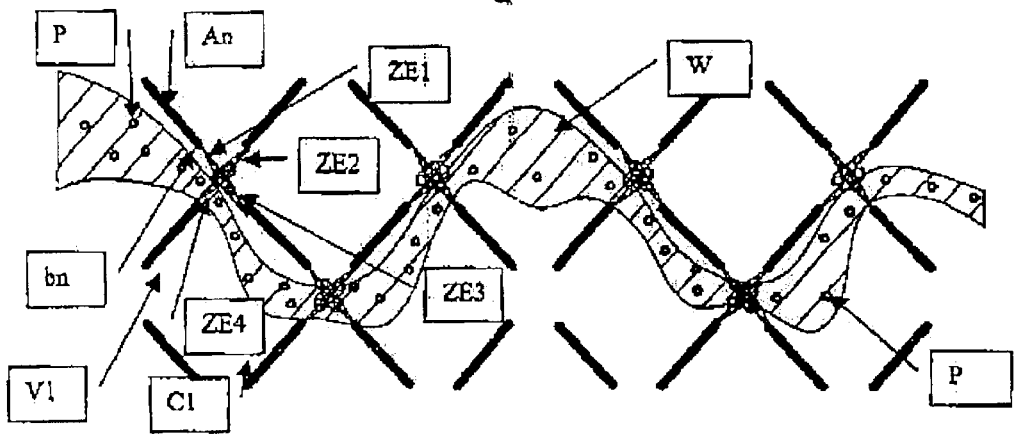
FIGS. 14 to 19 show, diagrammatically, and very simplified so that they can be understood easily (in two dimensions), the geometric structure and the electrostatic field structure met by an air flux passing through an electrostatic module according to the invention.
Figure 18:
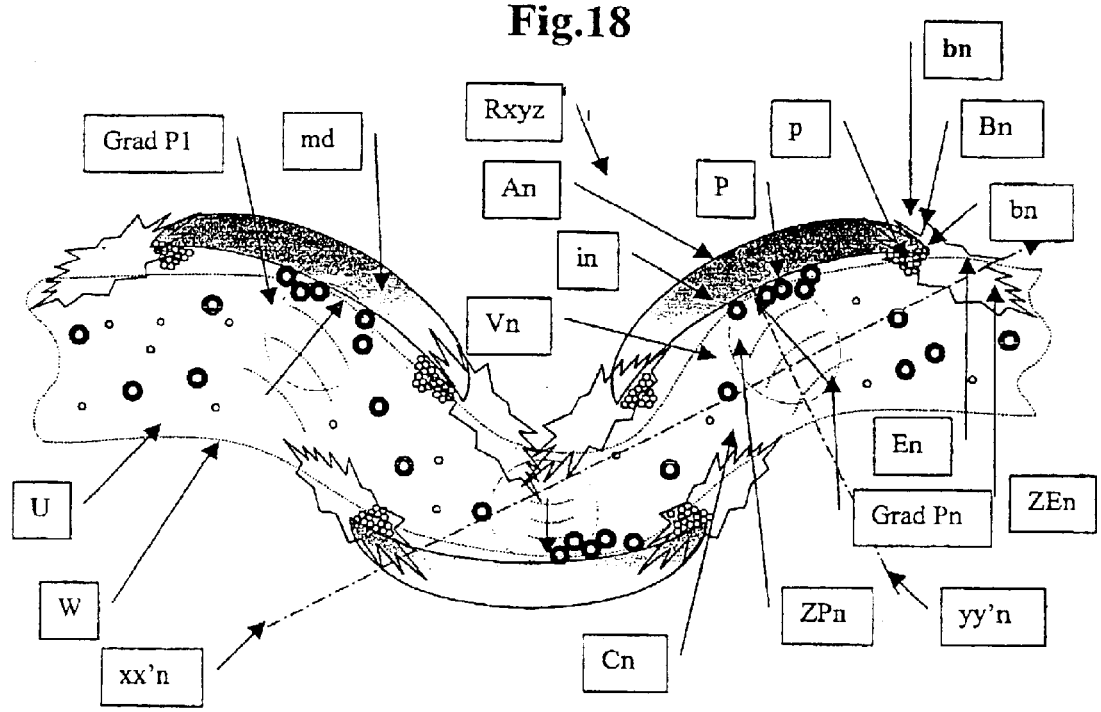

With reference to FIGS. 14 and 18, a very simplified diagram is provided (in two dimensions) of the action of an electrostatic generator 1 according to the invention, on the stream W of a portion of air flux loaded with particles P crossing the electrostatic module 2. It is understood that the symbolisation used in two dimensions is not strictly representative of reality but provides a visually understandable approach. The measures taken and electromagnetic calculations show that in the interior of the electrostatic module 2 there is a three-dimensional plurality of electrostatic induction zones, (ZE)=(ZE1, ZE2, ZE3, ZE4, . . . ZEn), distributed over a three-dimensional network, closely around the cell volumes (V1, . . . ) and in the vicinity of the trailing edges bn of the fins.

A three-dimensional representation of the field structure (E1, E2, E3, E4, . . . ) in the electrostatic induction zones (Z1, Z2, Z3, Z4, . . . ) in the vicinity of a recess of cell C1 is given in FIG. 5.

Figure 15:
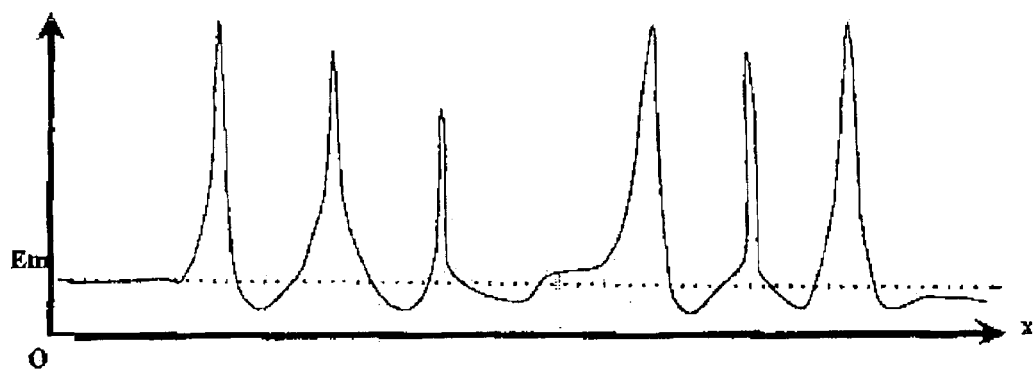

The potential difference between the electrodes 4, 5 induces significant polarisation of the dielectric md constituting the electrostatic module 2. As shown diagrammatically in FIGS. 14 and 15, it was shown by measurement that the combination between three-dimensional repetitiveness and the shape, externally convex and internally concave and compact of the cells C1 of the network Rxyz of fins An induced an unexpected result under the effect of this electrostatic polarisation. As shown in FIG. 15, along a stream W one notes high local variations in amplitude of the electrostatic field E through the dielectric material md and thus on the path of the stream W, relative to the average intensity Em evaluated over the totality of the electrostatic module 2. With a voltage between electrodes 4, 5, of B−=−5000 V and B+=+5000 V, that is with a potential difference of 10000 volts, and for an electrostatic module 2 of thickness of 1 cm, the average field Em has an average intensity of about 10000 V/cm. Inside the electrostatic module 2 according to the invention, it was calculated and measured that the electrostatic field (E1, E2, . . . ) in the vicinity of the points constituted by the trailing edges bn of the fins An, reaches intensities of 300000 V/cm in the induction zones (ZE1, ZE2, . . . ) surrounding the trailing edges of these fins. Thus one obtains an effect of local amplification of electric field which is very high, by a factor greater than 30 times.

Figure 16:
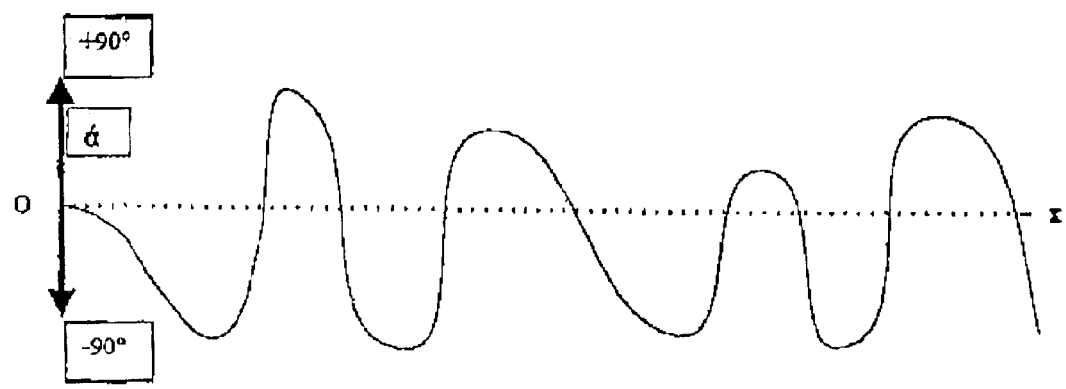

Another unexpected result appeared with reference to FIG. 16. Along the stream W one can note high variations of orientation ($\alpha$) of the electrostatic field E relative to the average orientation ($\alpha$=0) of the electric field evaluated over the totality of the electrostatic module 2. The orientation of the electric field E in the vicinity of the trailing edges bn covers practically all angular values (from −90° to +90°).

Figure 17:
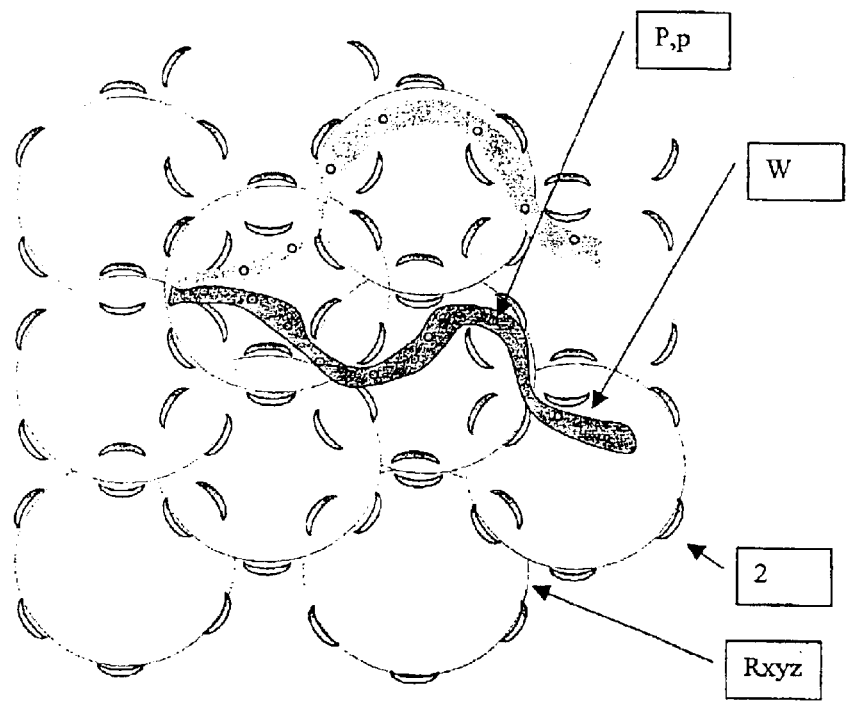
Figure 19:
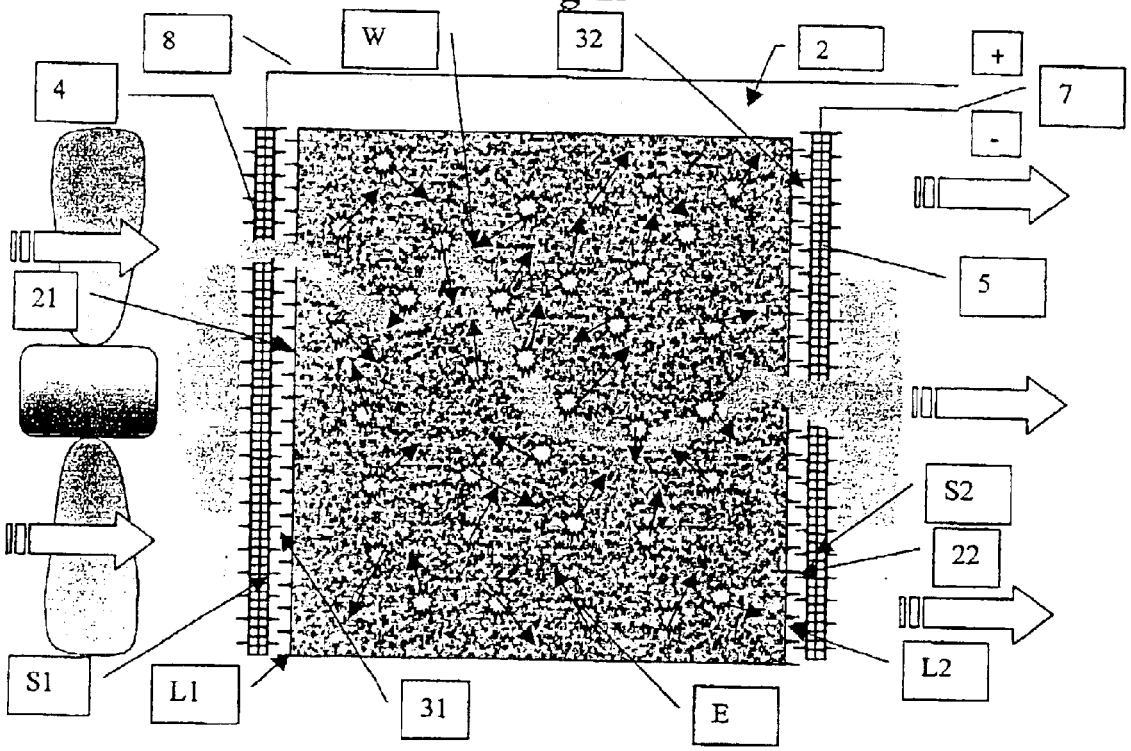

As described geometrically in FIGS. 17 and 18, and electrostatically in FIG. 19, the particles P,p of the streams W of fluid U thus undergo, when passing through the module 2, the action of an extremely chaotic field E, with considerably higher variations of intensity and orientation than in systems according to prior art.

According to a first preferred variant of the invention, shown in FIG. 4, the fins A13, A14, A15, also appearing in FIG. 5 and constituting the three-dimensional network Rxyz of the electrostatic module 2, have almost the same shape and the same dimensions.

Figure 9:
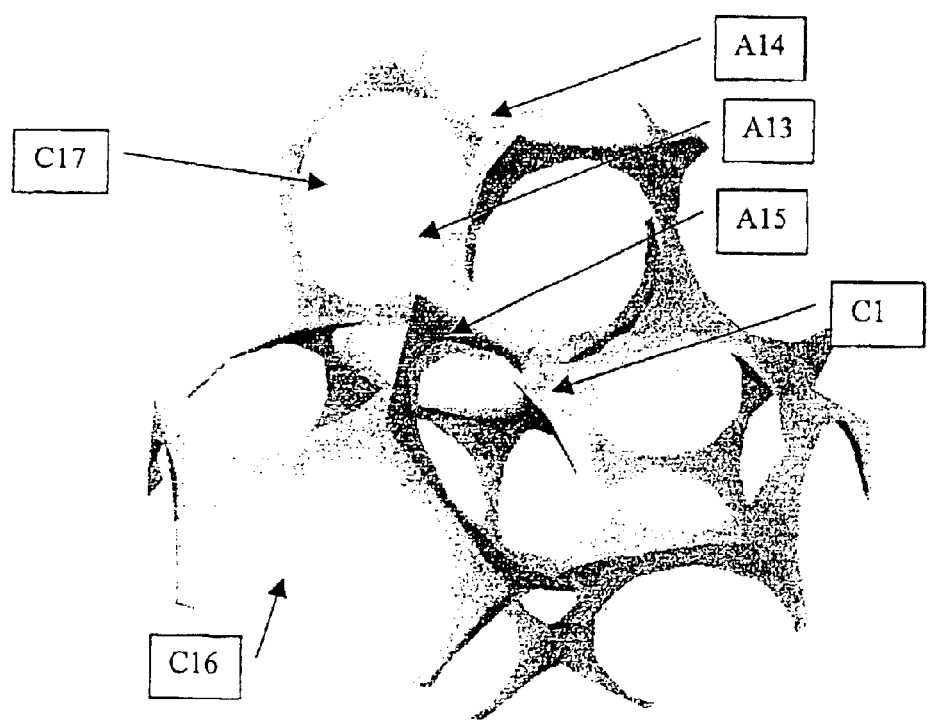
FIGS. 9 and 11 show another variant of the electrostatic module according to the invention, obtained by assembly of a polyhedral network (dodecahedrons) with pierced faces.
Figure 11:
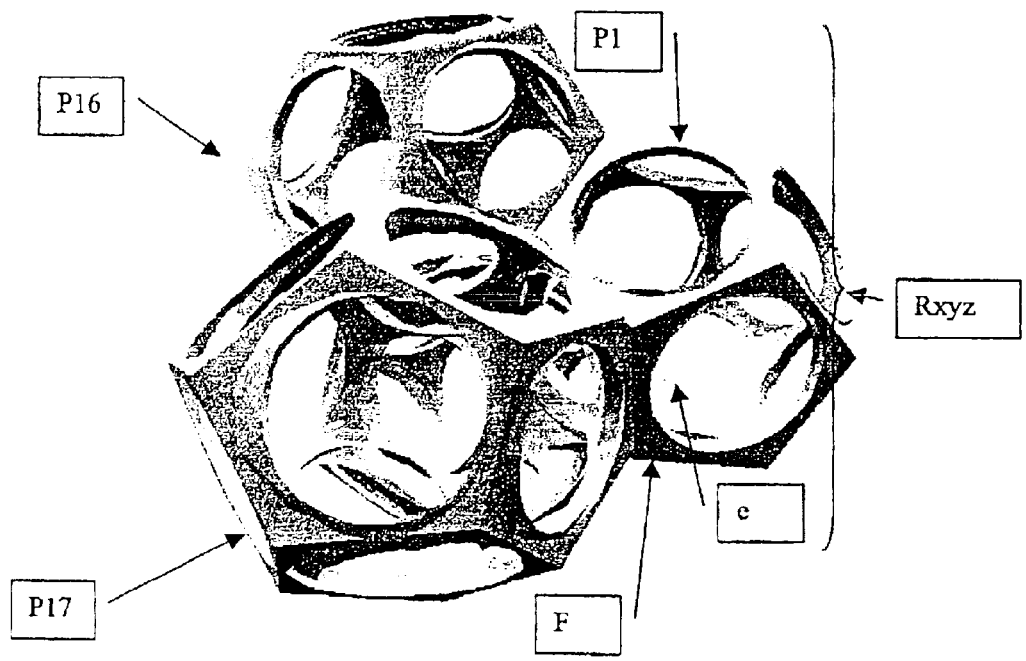

According to a second variant of the invention, shown in FIG. 9 and FIG. 11, the fins (A13, A15, . . . ) are connected in a three-dimensional network Rxyz, to meshes constituted of closely polyhedral cells (C1, C16, C17, . . . ) connected to each other. The inventors established that a dodecahedral structure gave excellent results.

According to a third preferred variant of the invention, shown in FIGS. 2 to 4, the recesses (e16, e17, e18, e19, . . . ) between the adjacent internal elementary volumes (C1, C16, C17, . . . ) of the electrostatic module 2 were, in the majority, closely circular or elliptical in shape.

According to a fourth preferred variant of the invention, also shown in FIGS. 2 to 5, the fins (A13, A14, A15, . . . ) constituting the three-dimensional network Rxyz of the electrostatic module 2 have relative longitudinal dimensions l and are physically connected to each other in a configuration such that the elementary surfaces (internally tangential to the fins) (S1, S16, S17, . . . ) of the interior cells (C1, C16, C17, . . . ) of the three-dimensional network Rxyz are closely in a closed quadratic shape (that is spherical or ellipsoidal). Thus the interior elementary empty cell volumes (V1, V17, . . . ) of the three-dimensional network Rxyz are closely of an empty convex shape in a ball or ovoid.

According to a fifth preferred embodiment of the invention, the fins of the three-dimensional network Rxyz of the electrostatic module 2 have relative longitudinal dimensions l and are physically connected to each other in a configuration such that the closed quadratic elementary surfaces (S1, S16, S17, . . . ) of the interior cells (C1, C16, C17, . . . ) of the network Rxyz are distributed closely according to their said geometry of greatest compactness, such as shown in FIGS. 4 and 5.

Figure 10:
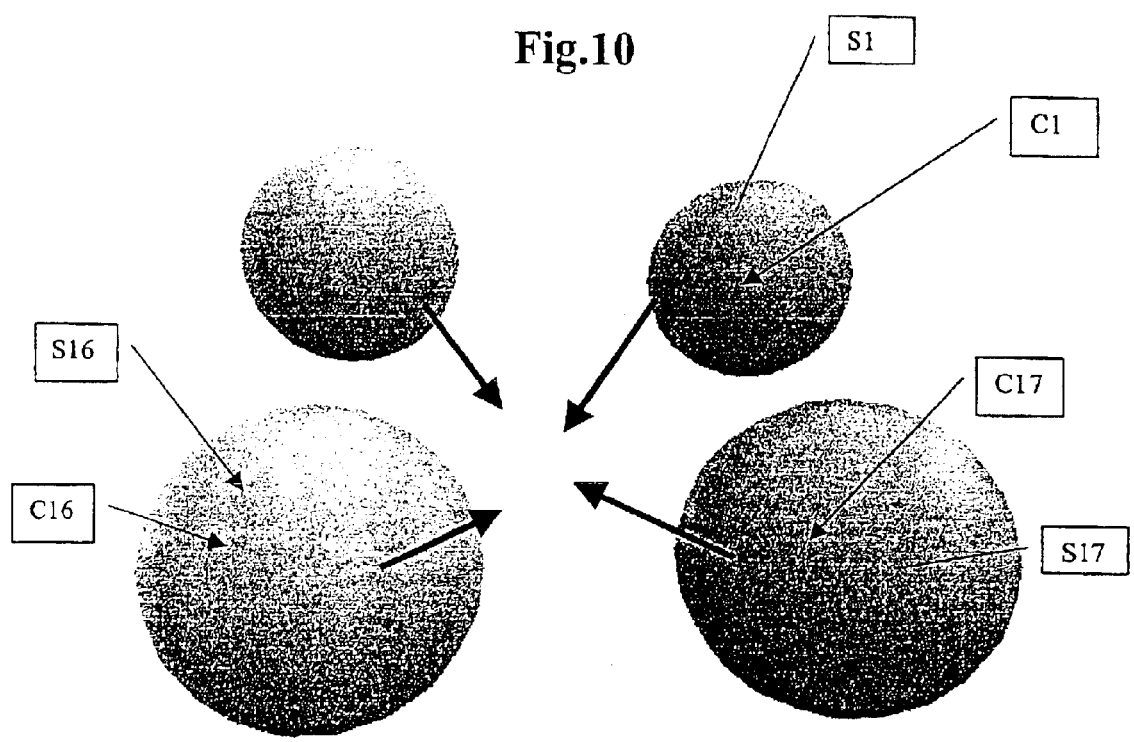

A method for implementation of the invention which seemed particularly simple is shown in FIG. 10. It consists of producing the three-dimensional network Rxyz by approach, intersection and union of closed quadratic shapes (C1, C16, C17, . . . ) of small thickness and in particular spheres or ellipsoids. This can be produced in particular by combination between a chemical action and a pressure action on a foam of plastic material in formation.

According to a sixth variant shown in FIG. 11, the three-dimensional network Rxyz is produced by, approach and union of globally polyhedral initially independent shapes (P1, P16, P17, . . . ) of small thickness, where the majority of faces F are pierced by a recess e. The polyhedrons (P1, . . . ) are assembled together, in physical contact, in such a way that their recesses e communicate.

According to a seventh preferred variant of the invention, shown in FIGS. 2 to 4, the fins (A13, A14, A15, A16, . . . ) constituting the three-dimensional network Rxyz of its electrostatic module 2 have relative longitudinal dimensions l and are physically connected to each other in a configuration such that the closed elementary surfaces (S1, S16, S17, . . . ) of the interior cells (C1, C16, C17, . . . ) of the network Rxyz are closely distributed such that a majority of the internal cellular elementary volumes (V1, . . . ) of the network Rxyz open up facing 12 elementary volumes (V16, V17, . . . ) of neighbouring cells (C16, C17, . . . ) through 12 recesses (e16, e17, . . . ) through their elementary surfaces (S16, S17, . . . ). The network can be produced in such a way that the cells are distributed approximately in a so-called "centred cubic face" shape.

The inventors established that advantageously, for implementing the invention, polyurethane could be used as dielectric material md constituting the fins (A13, A14, A15, . . . ) of the three-dimensional network Rxyz of the electrostatic module 2.

Figure 20:
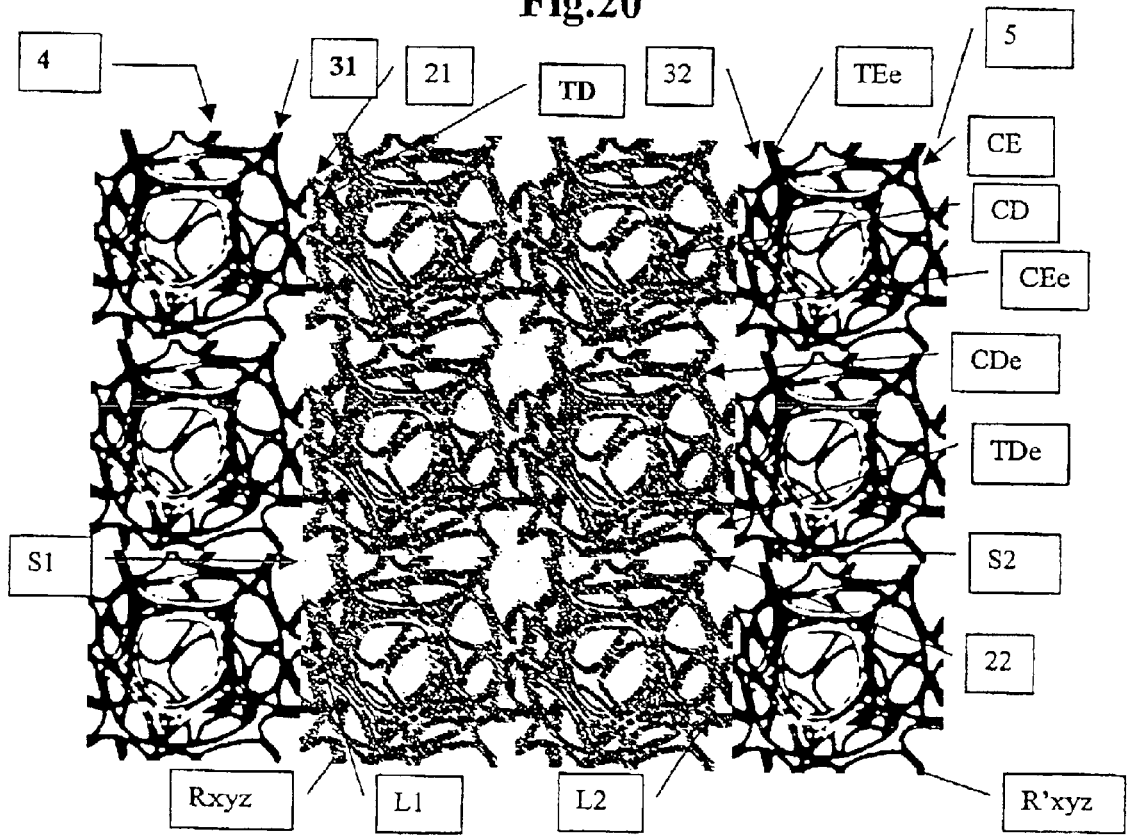
FIG. 20 shows, in transversal cross-section, and in a simplified manner (by enlarging the size of the network cells) a preferred embodiment variant for the production of the electrostatic module and the electrodes of the electrostatic module according to the invention.

According to an eighth preferred variant of the invention, the inventors established, by efficiency measurements of electrostatic amplification as shown in FIGS. 19 and 20, that preferably at least one of the lateral contact faces L1, L2 of the electrostatic module 2 (and preferably the two), in contact with a lateral support face S1, S2, corresponding to one of the electrodes 4, 5, should be covered in a closely uniform way with a plurality of sharp shapes TD with points 21, 22, with a small radius of curvature, distributed over this lateral face L1, L2. The points 21, 22 are in contact with the corresponding support face S1, S2 of the facing electrode 4, 5.

The inventors also established by measurements that, as shown in FIGS. 19 and 20, preferably at least one of the lateral support faces S1, S2, of at least one of the polarisation electrodes 4, 5 (and preferably the two), in contact with a lateral contact face L1, L2, of the electrostatic module 2, should be covered in a closely uniform way with a plurality of points 31, 32, distributed over this lateral support face S1, S2. These points 31, 32 are in contact with the corresponding contact face L1, L2, of the electrostatic module 2, and interact with the points 21, 22 of the electrostatic module 2.

It is shown by calculation and by measurement that, in this way, the local amplification effect of the magnetic field E is increased within the electrostatic module 2 together with the amplitude of local variation in intensity of the electric field Ei within the electrostatic induction zones ZE=(ZE1, . . . , ZEi, . . . ZEn, . . . ).

The inventors were able to establish that the efficiency of the electrostatic generator 1 increases and its loss of charge diminishes if, as shown in FIG. 20, the dielectric electrostatic module 2 and its conducting electrodes 4, 5, have the same cellular geometry.

According to this eighth preferred variant of the invention, the dielectric electrostatic module 2 and the conducting electrodes 4, 5, have the same geometry constituted of a network of thin and longilineal fins A13 connected by their ends A131 and distributed in three-dimensional networks Rxyz and R'xyz, such as shown in FIGS. 4 to 6. The fins of the two networks provide a multitude of cells CD, CE, communicating by recesses (e13, . . . ) and surrounding compact empty elementary cellular volumes V1, of transversal dimensions of the same order of size in the three directions dx, dy, dz. The dielectric electrostatic module 2 and the conducting electrodes 4, 5, have fins A13 of closely identical shape and dimensions l. Thus, the dielectric electrostatic module 2 and the conducting electrodes 4, 5, are constituted of cells CD, CE, of closely identical dimensions and geometry. They differ through their constitutive material (dielectric, conducting).

According to a ninth preferred variant of the invention described with reference to FIG. 20, it is established that the points 21, 22, of the lateral contact surface L1, L2, of the electrostatic module 2 are constituted by the section of a multitude of elementary cells CDe of the external wall of the three-dimensional network Rxyz, distributed over the surface of at least one of the lateral faces L1, L2, and providing, at right angles to each external cell CDe sectioned, a multitude of nozzles TDe, with pointed edges 21, 22, closely circular in shape facing the corresponding lateral support face S1, S2. In the same way, the points 31, 32, of the lateral support surface S1, S2, of at least one of the electrodes 4, 5, (and preferably the two) are furthermore constituted (as for the case of the electrostatic module) by the section of a multitude of elementary cells CEe of the external wall of the three-dimensional network R'xyz of this electrode 4, 5, distributed over the surface of at least one of the lateral support faces S1, S2. These sections provide, at right angles to each external cell CEe sectioned, a multitude of metallic nozzles TEe, with pointed edges 31, 32, closely circular in shape, located facing the corresponding lateral contact face L1, L2.

The method recommended for manufacturing amplification metallic electrodes 4, 5, for constituting the volume generator 1 of the electrostatic field according to the invention consists of producing first of all a primary network R1xyz, dielectric or semiconducting. This network R1xyz is identical to that shown in FIGS. 4 to 9. It is formed of a plurality of fins A13 constituted of a dielectric md or semiconducting material. The fins A13 of the network R1xyz have a thin transversal cross-section St, of thickness e very much smaller than their longitudinal dimension l. They comprise at least one lateral trailing edge bn, elongated and tapered (that is, with a small local transversal radius of curvature) oriented in the direction xx' of their length. The fins A13 of the network R1xyz are physically and electrically connected to each other by each of their ends A131 to constitute a three-dimensional network R1xyz. They are associated and regrouped geometrically into a multiplicity of elementary cells C1. The majority of associated fins A13, belonging to a same cell C1 interior to the network R1xyz, surround and juxtapose, by at least one of their lateral longitudinal faces, an interior virtual elementary surface S1 of closed geometry, to include an empty elementary cellular volume V1, compact and convex. The elementary cellular volume V1 of the majority of the cells C1 located at the centre of the network R1xyz opens out facing elementary volumes of neighbouring cells by at least four, and preferably twelve, recesses E through their elementary surface S. Each of these recesses E is surrounded by the lateral edge of fins belonging to its cell and common to the neighbouring cells.

In order to produce the primary network R1xyz, one proceeds preferably by intersection of a multitude (preferably twelve) of material closed surfaces S=(S1, . . . , Si, . . . , Sn, . . . ) with an envelope 2 of small thickness e, distributed closely uniformly in the 3 directions x, y, z, and made of a first material 11, dielectric and in particular constituted of polyurethane.

Then electroplating of a second metallic material mc is carried out, in particular nickel, on the primary network R1xyz. Thus a three-dimensional network R2xyz is produced with an external metallic surface.

The invention recommends producing these electrodes 4, 5, by nickel electroplating on a polyurethane network R1xyz.

The method consists, first of all of producing a porous network plate R1xyz with wings in polyurethane according to the invention as shown in FIGS. 4 to 9. Then one provides the polyurethane network R1xyz with electric conductivity by plunging it into a sensitisation solution of the type: $SnCl_1$ –25 gm/l; HCl –40 ml/l. The network R1xyz is kept in the solution for 10 minutes, and then washed in hot water for 10 minutes. After this, the network R1xyz is plunged for 5 minutes into a tank containing an activation solution of the type: $PdCl_1$ –0.5 gm/l; HCl –10 ml/l. Next, it is washed in hot water for 10 minutes.

Then a chemical layer of nickel is deposited on the network R1xyz. In order to do this the network is plunged into a solution of the type (in ml/l):

| | |
|---|---|
| $NiSO_4.7H_2O$ | 25 |
| $NaH_2PO_2.H_2O$ | 25 |
| $NaP_2O_7.10H_2O$ | 50 |
| $NH_4OH$ (28% sol) | 23 |

The network R1xyz is kept in the solution for 30 minutes. The it is washed in water for 10 minutes.

Next, electroplating with nickel is carried out. To do this, two anodes of nickel are placed in an electrolysis bath. The network R1xyz is set between the two anodes in the bath. The bath is filled with a solution with a composition of the type (in gm/l):

| | | | |
|---|---|---|---|
| $NiSO_4.7H_2O$ | –250 | 1,4 butandiol | 0.15 |
| $NiCl_2$ | 50 | Phthalamide | 0.12 |
| $H_3BO_3$ | 30 | pH | 4.3–5.1 |

The anodes and the network R1xyz are connected to the different poles of a direct current generator. (Anodes to the positive pole, network R1xyz to the negative pole) The intensity of the deposit current is adjusted to 0.5 $A/dm^2$ for 7–10 minutes. 10 successive electroplating cycles are carried out.

After metallic electroplating of the conducting material mc, extraction of the skeleton constituted of the subjacent dielectric material md is carried out by calorific or chemical action on the external metallic surface of the three-dimensional network R2xyz. Thus, an entirely metallic structure R'2xyz is produced. Preferably, the subjacent structure in polyurethane is withdrawn by thermal effect. In order to carry this out, the network covered with nickel is placed in a reducing atmosphere at a temperature of 1100° C. for 4 hours. The network, R2xyz, is then ready.

Figure 21:
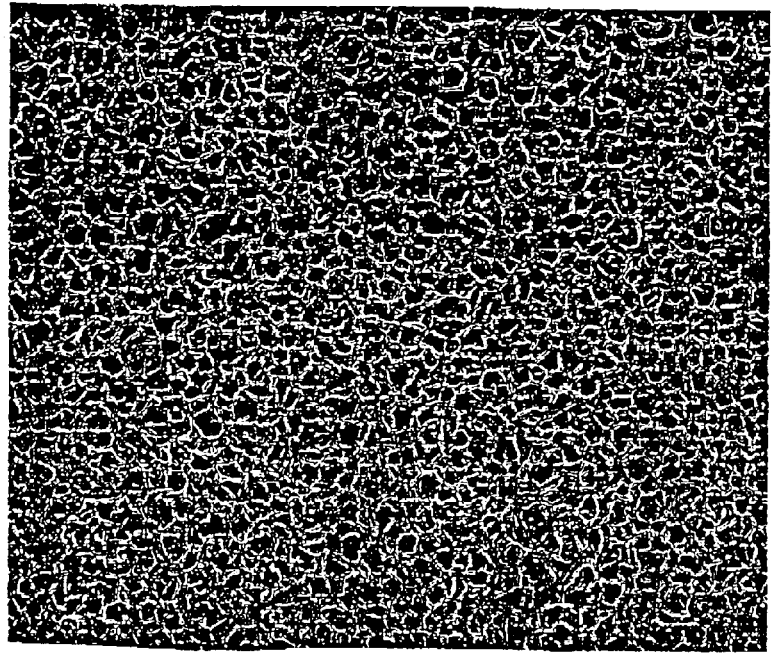
FIGS. 21 and 22 show the external view of a preferred variant of an electrostatic module and electrodes according to the invention.
Figure 22:
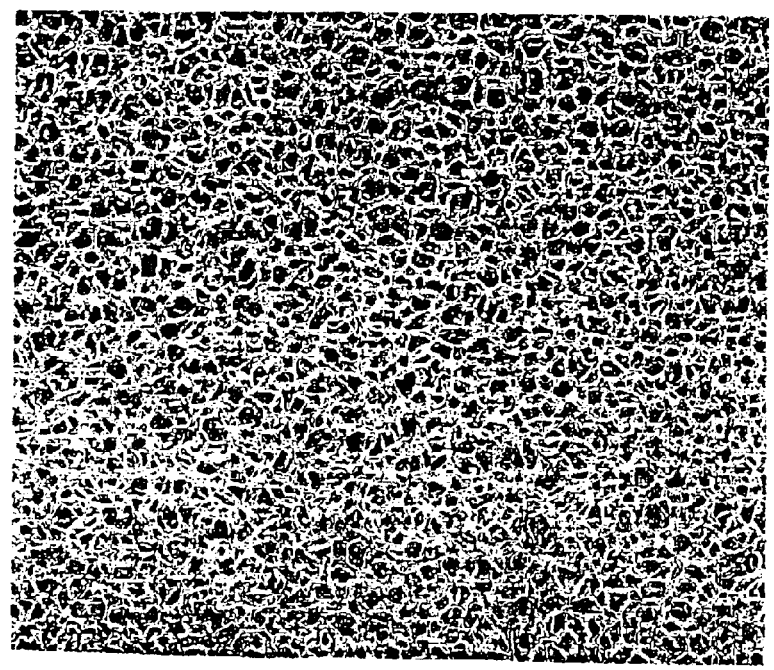

According to an eleventh preferred variant of the invention, shown in FIG. 20, the electrostatic module is constituted of a network Rxyz with polyurethane fins and the electrodes are constituted of a network R'xyz with initial base in polyurethane, metallized later, according to the above method. The internal geometry of the cells CD of the electrostatic module 2 and those CE of the electrodes 4, 5, is identical and in conformity with that given in section in FIG. 8. The geometry of the external surface S1, S2, of the network R2xyz of the electrodes 4, 5, and that L1, L2, of the network Rxyz of the module 2 is quasi-identical. This is seen by referring to FIGS. 21 and 22.

The networks Rxyz and R'xyz are constituted of cells C with closely polyhedral structure (dodecahedral) whose internal cavity is in the shape of an elongated sphere (ellipsoidal). The principal axes of the cells C are closely oriented in the same direction. The average ratio between the dimensions D11 and D12 of the ellipsoids along their principal perpendicular axes is about 1.1–1.3. The cells are positioned according to their greatest density distribution and have twelve neighbouring cells. They are pierced by twelve recesses.

Figure 12:
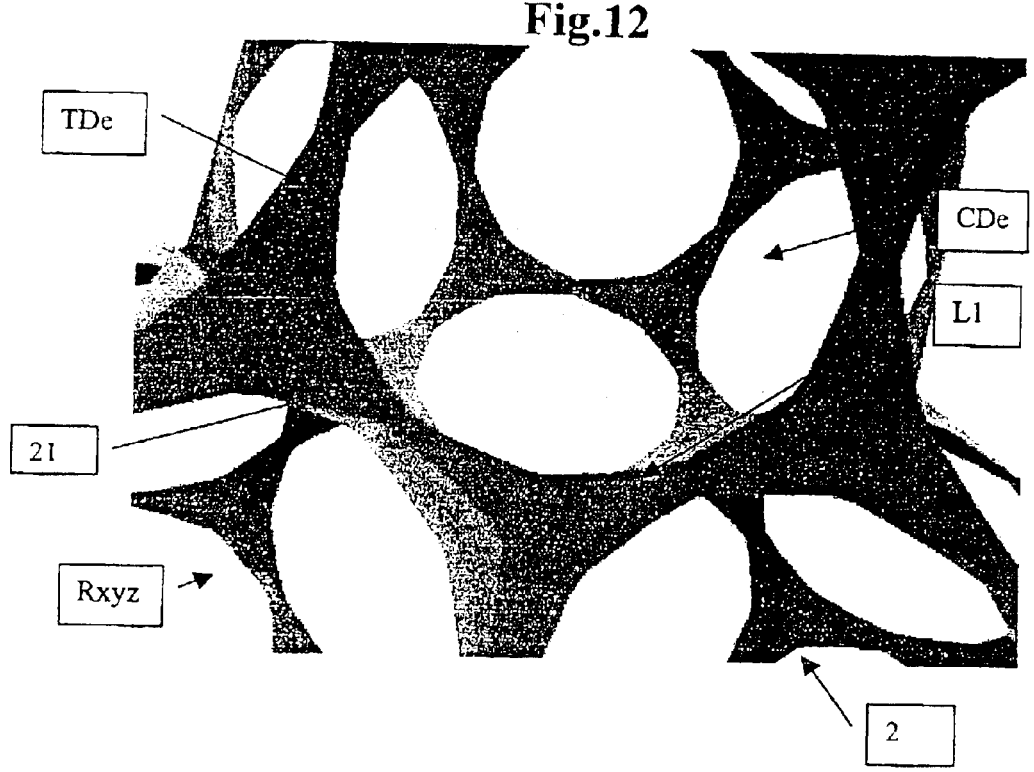
FIGS. 12 and 13 show, in perspective, the lateral wall and the interior of the network of an electrostatic module according to the invention.
Figure 13:
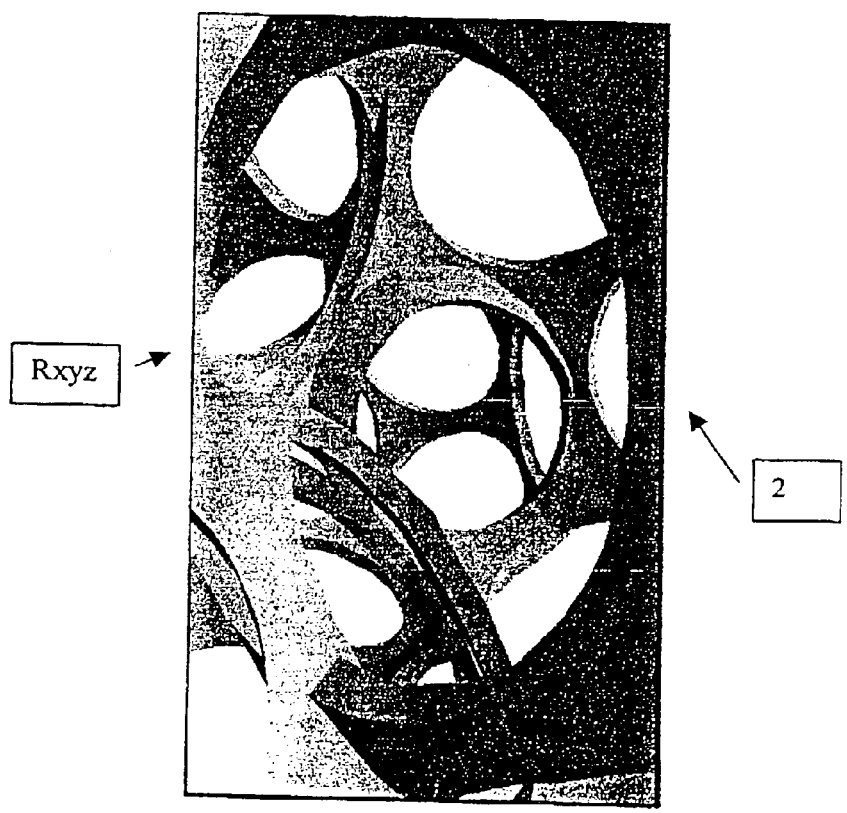

FIG. 12 shows, in enlarged form, an external portion of the lateral contact face L1 of the electrostatic module 2. It can be seen that the points (in nozzles) 21, 22, of the lateral contact surfaces L1, L2 of the electrostatic module 2 are constituted by section of a multitude of elementary cells CDe of the external wall L1 of the three-dimensional network Rxyz. These sectioned parts are distributed over the surface of at least one of the lateral faces L1, L2, and provide a multitude of nozzles TDe at right angles to each sectioned external cell CDe, with pointed edges 21, 22, of closely circular shape facing the corresponding lateral support face S1, S2, of the electrodes.

The operation of the generator 1 will be better understood with reference to FIG. 18. The stream W of flux F passes across the network Rxyz of the electrostatic module 2 through a high number (more than 3) of alternate linked successions, on the one hand of fields of local pressure gradients, grad Pn, on the lower surface, in, of the fins An of the network Rxyz, and on the other hand of local electrostatic field gradients En on the trailing edges bn. The local pressure gradients, grad Pn, create local impact zones ZPn, surrounding points An of pressure action. These are distributed sequentially (in network) along the external surface of the stream W. The majority of these areas are located on the lower surface, in, of the fins An, and the majority of the biggest particles P are deposited here and adhere locally to the material md by Van der Waals forces.

The local electrostatic field gradients En are mainly raised locally within the electrostatic induction zones ZEn, surrounding points Bn of electrostatic action located on the trailing edges, bn. These are also distributed sequentially (in network) along the external surface S of the stream W.

It can be seen that the points Bn of electrostatic action are located in a geometric position staggered transversally relative to the points An of corresponding pressure action, both according to the overall average local direction, xx'n, of the flux U and according to the local direction, yy'n, perpendicular to the flux U.

The stream of fluid W surrounding the particles P,p is thus submitted first of all to the local action of the pressure gradient, grad Pi, located upstream of the flow, with a view to deflecting it, before entering the electrostatic induction zone ZEn, located further downstream.

Advantages of the Invention Relative to Prior Art

A first advantage of the generator 1 according to the invention is that it ensures amplified recurrent multi-localised electrostatic induction and selective filtration, according to their size, of aerosol particles P,p within a flow F of carrier fluid U.

A second advantage of the invention is that, at the level of each cell Cn, it carries out selective filtration of big particles P of high mass, by preferential impact at'the level of the impact surfaces Zpn, before carrying out a physical electrostatic action (and particularly a filtration or chemical action) on the small particles p of low mass, through preferential electrostatic attraction at the level of the electrostatic induction zones ZEn. This means that the generator 1 according to the invention ensures better spatial selectivity for action on particles depending on their size.

A third advantage of this arrangement is that the big particles P tend to be deposited mainly in the "passive" zones of the central part of the lower surface, in, of the fins An and in the interior volume Vn of the cells Cn, thus in zones different from the "active" electrostatic induction zones, ZEn. The internal volume of the cells is such that the capacity for accumulation of big particles P is high. Thus the electrostatic generator 1 according to the invention is less likely to be blocked by big particles P than in systems according to prior art. The efficiency of electrostatic action is more stable. The length of time between servicing is greater.

A fourth advantage is that the high amplification effect of the electrostatic field of the generator 1 according to the invention allows higher physical action on the small particles p, which is not possible with systems of prior art. Moreover, an unexpected advantage has been established, that is that the physical efficiency of an electrostatic generator 1 according to the invention increases considerably when the size of the particles p becomes lower than 1 micron.

A fifth advantage of the generator 1 according to the invention is that, for equal efficiency of an equivalent system according to prior art, and from the fact that it amplifies the electrostatic field effect, it can have bigger cells; thus its loss of charge and energy consumption are lower.

A sixth advantage of the generator according to the invention is the fact that its physical action on the particles p,P is carried out more in-depth. This increases the efficiency and reduces the speed of clogging by the big particles.

A seventh advantage of the generator according to the invention is that, from the fact that the big particles P have little influence on the electrostatic induction zones Zen, the physical action is almost constant. Greater reliability is thus obtained and less loss of performance with time. Thus a generator according to the invention can be used without special servicing for a period of 5 years in a classic atmosphere of areas where the aerosol density is lower than 1 $mg/m^3$.

Finally, an eighth advantage of the generator according to the invention is that the zones Zen with high electrostatic field gradient are very concentrated. This means that for equivalent efficiency, a generator according to the invention generates less ozone than a system according to prior art.

Industrial Applications of the Invention

An electrostatic generator according to the invention can be used advantageously in all applications where it is appropriate to submit aerosol particles, and in particular very fine particles within a fluid, to intense electrostatic action, in order to obtain a physical, chemical, etc. result.

A current application consists of advantageously replacing all types of electro-filter, obtaining higher performance with less electricity consumption and efficiency which is greater and more stable for particles of sizes lower than 1 micron. Then one achieves performances equivalent to a ULPA filter but with greater reliability.

An unexpected application of the electrostatic generator according to the invention is linked to its destructive action of weak chemical bonds. Private tests carried out recently by the Russian Institute of biological problems with the participation of the European Space Agency and the Japanese Space Agency have shown very high action of the generator according to the invention on the destruction of noxious molecules located in the air. It was demonstrated, following tests practised on the electrostatic generator according to the invention, operating at 10000 V and used for 30 days in a volume of 300 $m^3$, that the concentration of certain noxious gaseous molecules in the air varied in the following way:

| Gaseous molecule | Limit | Initially | After 30 days |
| --- | --- | --- | --- |
| CO | 10.0 | 2 | 0 |
| Ammonia | 1.0 | 0.2 | 0 |
| Acetone | 1.0 | 0.33 | 0.12 |
| Methanol | 0.2 | 0.034 | 0 |
| Isopropyl alcohol | 1.5 | 0.26 | 0 |
| Benzol | 0.2 | 0.011 | 0 |
| Toluol | 8.0 | 0.06 | 0.01 |

Such tests have provided practical confirmation of the high level of energy liberated at the level of the amplified electrostatic field zones within the electrostatic module, such that it enables destruction of the chemical bond.

An application which can be envisaged is the chemical destruction by electrostatic method of noxious molecules and an action on free radicals in the air.

The range of the invention must be taken into consideration in relation to the following claims and their legal equivalents, more than by the examples given above.

What is claimed is:

1. Volume generator (1) of chaotic electrostatic field (E=E1, E2, E3, . . . ), amplified locally, to submit a fluid (U) loaded with aerosol particles (P,p) to the action of an electrostatic field (E) with high local variation of amplitude and orientation, this generator (1) comprising:

a) an induced electrostatic module (2);
  constituted of a dielectric or semiconducting material (md),
  generally flat in shape,
  with porous geometry and permeable to the passage of fluids (U),
    constituted of a network in three-dimensional meshes (Rxyz),
    each mesh of the network being constituted of an elementary convex cell, recessed and concave at its centre to include a compact elementary empty cellular volume (V1), of transversal dimensions (dx1, dy1, dz1) of the same order of size in the three dimensions (x, y, z,),
    and in which the elementary empty cellular volume (V1) of the majority of cells (C1) located at the centre of the electrostatic module (2) opens out facing elementary empty volumes (V16, V17, . . . ) of neighbouring cells (C16, C17, . . . ), by at least four recesses (e16, e17, e18, e19) through their elementary surface (S16),
  having on either side at least two lateral contact surfaces (L1, L2,) facing each other, b) two electrostatic induction electrodes (4, 5),
  constituted of a conducting material (mc),
  generally flat in shape,
  with porous geometry and permeable to the passage of fluids (U),
  placed facing each other, separated from each other, on either side of the electrostatic module (2), and
  each co-operating by one of their lateral support faces (S1, S2) with one of the two lateral contact faces (L1, L2) of the polarisable module (2), c) a source of electric current (6) comprising at least two metallic terminals (B+, E−) with a significantly high electric potential difference between them, d) two conductors (7, 8),
  each connected by one end (9, 10) to one of the potential difference terminals (8+, B−) and/or the earth, and at the other end (11, 12) to one of the different polarisation electrodes (4, 5),
  for generating between the two electrodes (4, 5) and thus in the interior of the polarisable module (2), a distribution of charges (q) over the surface (Sd) of its constitutive material (md) and consequently a volume distribution of the internal electric field (E),
  one of the two conductors (9) able to be constituted partially by the earth (G), e) a means (3) for putting fluid into overpressure to ensure its flow through the electrodes (4, 5) and the electrostatic module (2);

this volume generator (1) of chaotic electrostatic field (E) being characterized in that furthermore its electrostatic module (2) is constituted of a plurality of fins (A=A1, A2, . . . , An, . . . ) with longilineal portions, constituted of a dielectric or semiconducting material (md):

A. where the fins (An) have a thin transversal cross-section (St), of thickness (e) very much lower than their longitudinal dimension (l), and comprising at least one lateral trailing edge (bn) elongated and tapered (that is with small local transversal radius (Rn) of curvature) oriented in reaction (xn, x'n) of the length of the fins (An), B. where the fins (A1, . . . A13, A14, A15, . . . An, . . . ) are physically and electrically connected to each other by each of their ends (A13_1, A13_2, A14_1, A15_1, . . . ) to constitute a dielectric three-dimensional network (Rxyz), and are associated and regrouped geometrically to constitute a multiplicity of elementary cells (C1, . . . , C16, C17, . . . ) showing, locally at least, a three-dimensional periodicity (or pseudo-periodicity) in at least three directions (0x, 0y, 0z), C. where the majority of fins (A13) interior to the electrostatic module (2) are common to several elementary cells ( . . . , C1, . . . , C17, . . . ), D. where the majority of associated fins (A13, A14, A15, . . . ) belonging to a same cell (C1) interior to the electrostatic module (2) surrounding and juxtaposing tangentially, by at least one of their lateral longitudinal faces (s1 13/1, s1 14/1, s1 15/1, . . . ), a virtual elementary surface (S1) appropriate and interior to each elementary cell (C1) with closed geometry, to include a compact elementary empty cellular volume (V1), that is of transversal dimensions (dx1, dy1, dz1) of the same, order of size in the three directions (x, y, z);

E. where the elementary empty cellular volume (V1) of the majority of cells (C1) located at the centre of the electrostatic module (2) opens out facing the elementary empty volumes (V16, V17, . . . ) of neighbouring cells (C16, C17, . . . ) by at least four recesses (e16, e17, e18, e19) through their elementary surface (S16), F. and where each of the recesses (e16) is surrounded by the lateral edge (b161, b162, b163, . . . ) of fins ( . . . , A15 . . . ) belonging to its cell (C16) and common to the neighbouring cells (C16, C17, . . . );

such that the generator (1) comprises within its electrostatic module (2), a three-dimensional plurality of electrostatic induction zones, (ZE)=(ZE1, ZE2, ZE3, ZE4, . . . , ZEn) distributed over a three-dimensional network, closely around the cellular volumes (V1)

and in the vicinity of the trailing edges (bn) of the fins, and presenting locally:

high local variations of amplitude of the electrostatic field (E) relative to the average intensity (Em) evaluated over the totality of the electrostatic module (2), and/or high orientation values α of the electrostatic field (E) relative to the average orientation (α=0) of the electric field evaluated over the totality of the electrostatic module (2).

2. Volume generator (1) of electrostatic field according to claim 1, characterised in that the fins (A13, A15) constituting the three-dimensional network (Rxyz) of its electrostatic module (2) have closely the same shape and the same dimensions.

3. Volume generator (1) of electrostatic field according to claim 1, characterised in that the fins (A13, A15, . . . ) are connected in a three-dimensional network (Rxyz) with meshes constituted of cells (C1, C16, C17, . . . ) closely polyhedral.

4. Volume generator (1) of electrostatic field according to claim 1, characterised in that the recesses (e16, e17, . . . ) between adjacent internal elementary volumes (C1, C16, C17, . . . ) of its electrostatic module (2) are, in the majority, of closely circular or elliptic shape.

5. Volume generator (1) of electrostatic field according to claim 1, characterised in that the fins (A13, A14, A15, . . . ) constituting the three-dimensional network (Rxyz) of its electrostatic module (2) have relative longitudinal dimension (l) and are physically connected to each other in a configuration such that the elementary surfaces (internally tangential to the fins) (S1, S16, S17, . . . ) of the internal cells (C1, C16, C17, . . . ) of the three-dimensional network (Rxyz) are closely of closed quadratic shape (spherical or ellipsoid), such that the internal elementary empty cells (V1, V17 . . . ) of the three-dimensional network (Rxyz) are of a closely ball or ovoid empty shape.

6. Volume generator (1) of electrostatic field according to claim 5, characterised in that the fins (A13, A14, A15, . . . ) constituting the three-dimensional network (Rxyz) of its electrostatic module (2), have relative longitudinal dimensions (l) and are physically connected to each other in a configuration such that the closed quadratic elementary surfaces (S1, S16, S17, . . . ) of the internal cells (C1, C16, C17, . . . ) of the network are distributed closely according to their geometry of so-called greatest compactness.

7. Volume generator (1) of electrostatic field according to claim 6, whose three-dimensional network (Rxyz) is produced by approach, intersection and union of closed quadratic shapes (C1, C16, C17, . . . ) of small thickness and in particular spherical or ellipsoidal.

8. Volume generator (1) of electrostatic field according to claim 3, where the three-dimensional network (Rxyz) is produced by approach and union of globally polyhedral shapes (P1, P16, P17, . . . ) of small thickness, where the majority of faces (F) are pierced by a process (E), and assembled together in contact such that their recesses (E) communicate.

9. Volume generator (1) of electrostatic field according to claim 1, characterised in that the fins (A13, A14. A15, A16, . . . ) constituting the three-dimensional network (Rxyz) of its electrostatic module (2) have relative longitudinal dimensions (l) and are physically connected to each other in a configuration such that the closed elementary surfaces (S1, S16, S17, . . . ) of the internal cells (C1, C16, C17, . . . ) of the network (Rxyz) are closely distributed in such as way that a majority of the internal cellular elementary volumes (Vi, . . . ) of the network (Rxyz) open out facing 12 elementary volumes (V16, V17, . . . ) of neighbouring cells (C16, C17, . . . ) by 12 recesses (e16, e17, . . . ) through their elementary surfaces (S16, S17, . . . ).

10. Volume generator () of electrostatic field according to claim 1, characterised in that the constitutive dielectric material (md) of the fins (A13, A14, A15, . . . ) of th three-dimensional network (Rxyz) of its electrostatic module (2) is of polyurethane.

11. Volume generator (1) of electrostatic field according to claim 1, characterised in that at least one of the lateral contact faces (L1, L2) of the electrostatic module (2), in contact with a corresponding lateral support face (S1, S2) of one of the electrodes (4, 5), is covered almost uniformly with a plurality of sharp shapes (TD) with points (21, 22) with small radius of curvature, distributed over this lateral face (L1, L2) and in contact with the corresponding support face (S1, S2) of the facing electrode (4, 5), in such a way as to increase the local amplification effect of the electric field (E) within the electrostatic module (2) together with amplitude of local variations of electric field intensity (Ei) within the electrostatic induction zones (ZE)=(ZE1, . . . , ZEi, . . . , ZEn, . . . ).

12. Volume generator (1) of electrostatic field according to claim 11, characterised in that the points (21, 22) of the lateral contact surface (L1, L2) of its electrostatic module (2) are constituted by the section of a multitude of elementary cells (CDe) of the external wall of the three-dimensional network (Rxyz), distributed over the surface of at least one of the lateral faces (L1, L2), and providing at right angles to each sectioned external cell (CDe) a multitude of nozzles (TDe), with pointed edges (21, 22) of closely circular shape facing the corresponding lateral support face (S1, S2).

13. Volume generator (1) of electrostatic field according to claim 1, characterised in that at least one of the lateral support faces (S1, S2) of at least one of the polarisation electrodes (4, 5), (and preferably the two), in contact with a lateral contact face (L1, L2) of the electrostatic module (2), is covered almost uniformly with a plurality of points (31, 32) distributed over this lateral support face (S1, S2), these points (31, 32) being in contact with the corresponding contact face (L1, L2) of the electrostatic module (2), in such a way as to increase the local amplification effect of the electric field (E) within the electrostatic module (2) as well as the amplitude of local variations of intensity of the electric field (Ei) within the electrostatic induction zones (ZE)=(ZE1, . . . , ZEi, . . . ZEn, . . . ).

14. Volume generator (I) of electrostatic field according to claim 1, characterised in that its dielectric electrostatic module (2) and its conducting electrodes (4, 5) have the same geometry constituted of:

a network of fins (A13), thin and longilineal, connected by their ends (A131), distributed in three-dimensional networks (Rxyz), (R'xyz), and providing a multitude of communicating cells (CD, CE) by recesses (e13, . . . ) and surrounding compact empty elementary cellular volumes (V1), of transversal dimensions of the same order of size in the three directions.

15. Volume generator (1) of electrostatic field according to claim 14, characterised in that its dielectric electrostatic module (2) and its conducting electrodes (4, 5) have fins (A13) of closely identical dimensions (l).

16. Volume generator (1) of electrostatic field according to claim 1, characterised in that its dielectric electrostatic module (2) and its conducting electrodes (4, 5) are constituted of cells (CD, CE) of closely identical geometry and dimensions.

17. Volume generator (1) of electrostatic field according to claim 13, characterised in that the points (31, 32) of the lateral support surface (S1, S2) of at least one of its electrodes (4, 5) are furthermore constituted by the section of a multitude of elementary cells (CEe) of the eternal wall of the three-dimensional network (R'xyz) of this electrode (4, 5), distributed over the surface of at least one of the lateral support faces S1, 52 and providing at right angles to each external cell (CEe) sectioned, a multitude of metallic nozzles (TEe), with pointed edges (31, 32), closely circular in shape, located facing the corresponding lateral contact face (L1, L2).

18. Method for manufacturing metallic amplification electrodes (4, 5) to constitute the volume generator (1) of electrostatic field according to claim 15, said method being characterised in that:

A. first of all a dielectric or semiconducting primary network (R1xyz) is produced constituted of a plurality of fins (13) constituted of a dielectric (md) or semiconducting material, these fins (13) possessing a thin transverse cross-section (St), of thickness (e) much lower than their longitudinal dimension (l), and comprising at least one lateral trailing edge (bn), tapered and elongated, (that is with a small local transversal radius of curvature) oriented in the direction (xx') of their length, these fins (A13) being physically and electrically connected to each other by each of their ends (131) to constitute a three-dimensional network (R1xyz), and being associated and regrouped geometrically into a multiplicity of elementary cells (C1) where the majority of associated fins (A13), belonging to a same cell (C1) interior to the network (R1xyz), surround and juxtapose, by at least one of their lateral longitudinal faces, an interior virtual elementary surface (S1) of closed geometry, to include a compact empty elementary cellular volume (V1), that is to say with transversal dimensions of the same order of size in the three directions; where the elementary cellular volume (V1) of the majority of the cells (C1) located at the centre of the network (R1xyz) opens out facing elementary volumes of neighbouring cells by at least four recesses (E) through their elementary surface (S), and where each of these recesses (E) is surrounded by the lateral edge of fins belonging to its cell and common to the neighbouring cells;

B. and next, electroplating of a second metallic material (mc), is carried out on the primary network (R1xyz), in order to produce a three-dimensional network (R2xyz) with an external metallic surface.

19. Method according to claim 18 to manufacturing metallic amplification electrodes (4, 5) characterised in that, in order to produce the primary network (R1xyz), one proceeds by intersection of a multitude of material closed surfaces S=(S1, ... Si, ..., Sn, ... ), having an envelope (2) of small thickness (e), arranged almost uniformly in the 3 directions (x, y, z), and produced in a first material (11), and constituted by polyurethane.

20. Method according to claim 18 to manufacturing metallic amplification electrodes (4, 5) to constitute a volume generator (1) of electrostatic field, said method being characterised in that after metallic electroplating of the conducting material (mc) extraction of the skeleton, constituted by the subjacent dielectric material (md), is carried out through calorific or chemical action on the external metallic surface of the three-dimensional network (R2xyz), to constitute an entirely metallic network (R'2xyz).

* * * * *